(12) United States Patent
Sambe et al.

(10) Patent No.: US 10,149,809 B2
(45) Date of Patent: Dec. 11, 2018

(54) SKIN AGING INHIBITOR AND CONCENTRATE OF RESVERATROL 3-O-α-GLUCOSIDE

(71) Applicant: EZAKI GLICO KABUSHIKI KAISHA, Osaka (JP)

(72) Inventors: Haruyo Sambe, Osaka (JP); Kazuhisa Sugimoto, Osaka (JP)

(73) Assignee: EZAKI GLICO CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/302,889

(22) PCT Filed: Apr. 8, 2015

(86) PCT No.: PCT/JP2015/061013
§ 371 (c)(1),
(2) Date: Oct. 7, 2016

(87) PCT Pub. No.: WO2015/156328
PCT Pub. Date: Oct. 15, 2015

(65) Prior Publication Data
US 2017/0035674 A1 Feb. 9, 2017

(30) Foreign Application Priority Data

Apr. 9, 2014 (JP) ................................ 2014-080165

(51) Int. Cl.
| | | |
|---|---|---|
| A61K 31/7034 | (2006.01) | |
| A61K 8/60 | (2006.01) | |
| C07H 15/203 | (2006.01) | |
| A61Q 19/08 | (2006.01) | |
| A61Q 19/02 | (2006.01) | |
| A23L 33/105 | (2016.01) | |
| A61K 8/34 | (2006.01) | |
| A23L 2/52 | (2006.01) | |

(52) U.S. Cl.
CPC ............... *A61K 8/602* (2013.01); *A23L 2/52* (2013.01); *A23L 33/105* (2016.08); *A61K 8/34* (2013.01); *A61K 8/345* (2013.01); *A61K 31/7034* (2013.01); *A61Q 19/02* (2013.01); *A61Q 19/08* (2013.01); *C07H 15/203* (2013.01); *A23V 2002/00* (2013.01); *A61K 2800/782* (2013.01); *A61K 2800/91* (2013.01); *A61K 2800/92* (2013.01)

(58) Field of Classification Search
None
See application file for complete search history.

(56) References Cited

U.S. PATENT DOCUMENTS

2002/0051799 A1    5/2002   Pruche et al.

FOREIGN PATENT DOCUMENTS

| CN | 101991836 | * | 3/2011 | ......... A61K 36/9068 |
|---|---|---|---|---|
| JP | 64-38009 | A | 2/1989 | |
| JP | 2002-80372 | A | 3/2002 | |
| JP | 2005-281179 | A | 10/2005 | |
| JP | 2008-88123 | A | 4/2008 | |
| JP | 2010-535221 | A | 11/2010 | |
| JP | 2010-270012 | A | 12/2010 | |
| WO | 2009/017866 | A1 | 2/2009 | |
| WO | 2012/105706 | A1 | 8/2012 | |

OTHER PUBLICATIONS

Hu et al., "A New Acylated Stilbene Glycoside from Acanthopanax brachypus" Bull Korean Chem Soc (2009) vol. 30 No. 3 pp. 703-706.*
Zouboulis et al., "Clinical aspects and molecular diagnostics of skin aging" Clinics in Dermatology (2011) vol. 29 pp. 3-14.*
Merriam-Webster's Collegiate Dictionary, Tenth Edition, published 1998 by Merriam-Webster, Inc, p. 924.*
English abstract of CN101991836 (Published Mar. 2011) downloaded from STN database HCAPLUS.*
English machine translation of CN101991836 above (Mar. 2011) downloaded from translationportal.epo.org.*
Fontecave et al., "Using Evaporation-Induced Self-Assembly for the Direct Drug Templating of Therapeutic Vectors with High Loading Fractions, Tunable Drug Release, and Controlled Degradation" Chemistry of Materials vol. 25 pp. 4671-4678 (Year: 2013).*
Shim et al., "Enzymatic Preparation of Phenolic Glucosides by *Streptococcus mutans*" Bull Korean Chem Soc vol. 24 No. 11 pp. 1680-1682 (Year: 2003).*
Du et al., "Polydatin: A review of pharmacology and pharmacokinetics" Pharmaceutical Biology vol. 51 No. 11 pp. 1347-1354 (Year: 2013).*
International Search Report, dated Jul. 14, 2015, for International Application No. PCT/JP2015/061013, 3 pages. (English Translation).
Kim et al., "Oxyresveratrol and Hydroxystilbene Compounds," *The Journal of Biological Chemistry* 277(18):16340-16344, 2002. (6 pages).
Ohguchi et al., "Inhibitory Effects of Resveratrol Derivatives from Dipterocarpaceae Plants on Tyrosinase Activity," *Bioscience, Biotechnology, and Biochemistry* 67(7):1587-1589, 2003.
Shim et al., "Enzymatic Preparation of Phenolic Glucosides by *Streptococcus mutans*," *Bulletin of the Korean Chemical Society* 24(11):1680-1682:2003.
Torres et al., "Enzymatic Synthesis of α-Glucosides of Resveratrol with Surfactant Activity," *Advanced Synthesis & Catalysis* 353:1077-1086, 2011.

* cited by examiner

*Primary Examiner* — Eric Olson
(74) *Attorney, Agent, or Firm* — Seed IP Law Group LLP

(57) ABSTRACT

An object of the present invention is to provide an anti-skin aging agent that can prevent skin aging such as spots, dullness, wrinkles, sags, and skin roughness. It has been found that resveratrol 3-O-α-glucoside has remarkable anti-skin aging effects such as melanogenesis suppression, hyaluronidase inhibition, anti-oxidization, cell activation, sirtuin gene activation, matrix metalloproteinase suppression, and anti-inflammation, and thus, can be used as an anti-skin aging agent.

7 Claims, 1 Drawing Sheet

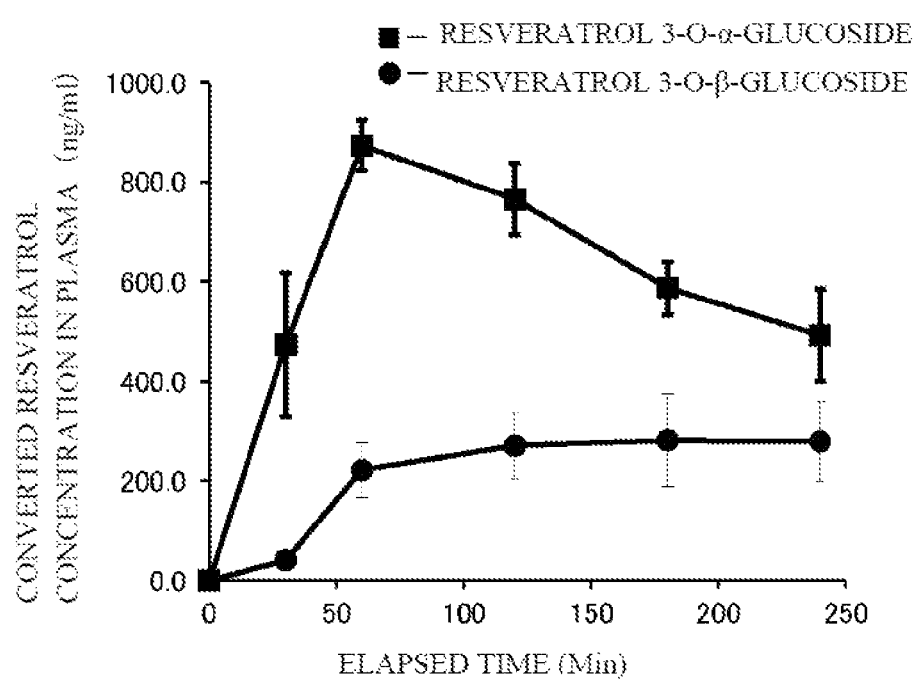

SKIN AGING INHIBITOR AND CONCENTRATE OF RESVERATROL 3-O-α-GLUCOSIDE

TECHNICAL FIELD

The present invention relates to an anti-skin aging agent that prevents skin aging through its effects such as melanogenesis suppression, hyaluronidase inhibition, anti-oxidization, cell activation, sirtuin gene activation, matrix metalloproteinase suppression, and anti-inflammation. The present invention also relates to a concentrate obtained by concentrating resveratrol 3-O-α-glucoside, which is used by being added to foods, cosmetics, medicines, and the like.

BACKGROUND ART

Resveratrol, which is a member of polyphenols contained in the skin of grapes, for example, is known as an antioxidant component. Resveratrol has also been reported to have physiological functions such as lifespan-extending, anti-cancer, and anti-microbial effects in various living organisms. Further, resveratrol has a melanogenesis suppressing effect, and thus, use of resveratrol in whitening cosmetics has been proposed (Patent Literature 1 and Non-Patent Literatures 1 and 2, for example). Since resveratrol has various functionalities as described above, resveratrol is now increasingly used not only in cosmetic products and foods but also in pharmaceuticals.

On the other hand, resveratrol has a problem in pharmaceutical formulation in that it is poorly soluble in water, and also has extremely poor stability. Thus, derivatization of resveratrol has previously been proposed to improve the water solubility and stability of resveratrol.

Patent Literature 2, for example, reported that β-glucosides (in particular, resveratrol 3-O-β-glucoside) of resveratrol exhibit increased water solubility and stability compared to resveratrol. While it is known that resveratrol 3O-β-glucoside exhibits a water solubility approximately 10-fold higher than that of resveratrol (Non-Patent Literature 3), it only has a water solubility of approximately 400 μg/mL. Thus, further improvement in water solubility is still desired. Moreover, resveratrol 3-O-β-glucoside has been reported to be inferior in tyrosinase inhibitory effect to resveratrol (Non-Patent Literatures 1 and 2), and thus, is also unsatisfactory in functionality.

Patent Literature 3 discloses that the use of resveratrol ethers such as resveratrol glucoside can improve the instability of resveratrol. Patent Literature 3 describes that resveratrol glucoside can be obtained by extraction from *polygonum cuspidatum* tissue or in vitro cultures of *vitis vinifera* cells. The resveratrol glucoside obtained by all of these methods is resveratrol 3-O-β-glucoside. The resveratrol glucoside disclosed in Patent Literature 3 is therefore also unsatisfactory in water solubility and functionality, as described above.

The resveratrol derivatives obtained in the conventional art are therefore still unsatisfactory in water solubility and functionality, although they have improved stability.

On the other hand, Non-Patent Literature 4 discloses obtaining resveratrol 3-O-α-glucoside through interaction of a solution containing resveratrol and sucrose with cells of *Streptococus mutans*. Non-Patent Literature 4, however, nowhere discusses the physical properties or characteristics of resveratrol 3-O-α-glucoside. It is known that generally in a glycoside, the physical properties and function of the aglycone per se are greatly affected by the bonded position or form of the sugar. Thus, Non-Patent Literature 4, which fails to disclose the physical properties or characteristics of resveratrol 3-O-α-glucoside, cannot be said to show applicability of resveratrol 3-O-α-glucoside.

Further, commercial production of products containing a resveratrol derivative will require using a concentrate of the resveratrol derivative as a raw material to be added. Resveratrol derivatives, however, have low water solubility, and the conventional art has not established a technique of concentrating a resveratrol derivative in a dissolved state to a high concentration. Thus, there is also a problem in that a resveratrol derivative cannot be prepared in the form of a concentrate.

In the modern society, consumers' growing interest in beauty has led to an increasing number of people who desire to maintain a healthy and youthful skin, regardless of age or sex. In the fields of cosmetic products, foods, medicines, and the like, therefore, the development of products for preventing skin aging such as spots, dullness, wrinkles, and sags is actively ongoing. In recent years, however, the consumer demand for performance in terms of skin aging prevention has continued increasing, and there is a need for the development of a novel anti-skin aging agent that can meet this consumer demand.

CITATION LIST

Patent Literature

Patent Literature 1: JP H01-38009 A
Patent Literature 2: JP 2002-80372 A
Patent Literature 3: JP 2010-535221 A

Non Patent Literature

Non Patent Literature 1: *J. Biol. Chem.*, 2002, 277, 16340
Non Patent Literature 2: *Biosci. Biotechnol. Biochem.*, 2003, 67, 1587
Non Patent Literature 3: *Adv. Synth. Catal.* 2011, 353, 1077
Non Patent Literature 4: *Bull. Korean Chem. Soc.* 2003, 24, 11, 1680

SUMMARY OF INVENTION

Technical Problem

An object of the present invention is to provide an anti-skin aging agent that can prevent skin aging such as sunburns, spots, dullness, wrinkles, sags, and skin roughness. Another object of the present invention is to provide a concentrate obtained by concentrating resveratrol 3-O-α-glucoside.

Solution to Problem

The present inventors conducted extensive research to solve the above-described problem, and found that resveratrol 3-O-α-glucoside has remarkable anti-skin aging effects such as melanogenesis suppression, hyaluronidase inhibition, anti-oxidization, cell activation, sirtuin gene activation, matrix metalloproteinase suppression, and anti-inflammation, and thus, can be used as an anti-skin aging agent. The inventors also found that resveratrol 3-O-α-glucoside in a dissolved state can be concentrated to a high concentration by mixing resveratrol 3-O-α-glucoside with a monohydric to tetrahydric alcohol with 1 to 6 carbon atoms. The present invention was completed by conducting further research based on these findings.

Specifically, the present invention provides aspects of invention as itemized below.

Item 1. An anti-skin aging agent containing resveratrol 3-O-α-glucoside as an active ingredient.

Item 2. The anti-skin aging agent according to item 1, which is used as a melanogenesis inhibitor or a whitening agent.

Item 3. The anti-skin aging agent according to item 1, which is used as a hyaluronidase inhibitor.

Item 4. The anti-skin aging agent according to item 1, which is used as an oxidative stress-reducing agent in skin tissue.

Item 5. The anti-skin aging agent according to item 1, which is used as a matrix metalloproteinase expression inhibitor.

Item 6. The anti-skin aging agent according to item 1, which is used as a cell activator for skin cells.

Item 7. The anti-skin aging agent according to item 1, which is used as a sirtuin gene expression promoter.

Item 8. The anti-skin aging agent according to item 1, which is used as an anti-inflammatory agent for suppressing skin aging.

Item 9. An external preparation for skin containing the anti-skin aging agent according to any of items 1 to 8.

Item 10. A preparation for oral cavity containing the anti-skin aging agent according to any of items 1 to 8.

Item 11. A food or beverage product containing the anti-skin aging agent according to any of items 1 to 8.

Item 12. A pharmaceutical for systemic administration containing the anti-skin aging agent according to any of items 1 to 8.

Item 13. Use of resveratrol 3-O-α-glucoside for manufacture of an anti-skin aging agent.

Item 14. Resveratrol 3-O-α-glucoside used in treatment for preventing skin aging.

Item 15. A method for preventing skin aging including the step of percutaneously or orally administering resveratrol 3-O-α-glucoside to a human in need of skin aging prevention.

Item 16. A concentrate of resveratrol 3-O-α-glucoside in which resveratrol 3-O-α-glucoside is contained in a solvent containing a monohydric to tetrahydric alcohol with 1 to 6 carbon atoms.

Item 17. The concentrate according to item 16, wherein the monohydric to tetrahydric alcohol with 1 to 6 carbon atoms is at least one selected from the group consisting of ethanol, propylene glycol, 1,3-butylene glycol, dipropylene glycol, 1,2-pentanediol, 1,2-hexanediol, and glycerol.

Item 18. The concentrate according to item 16 or 17, wherein the monohydric to tetrahydric alcohol with 1 to 6 carbon atoms is contained in an amount of 5 to 100 parts by weight per total amount of 100 parts by weight of the solvent.

Item 19. The concentrate according to any of items 16 to 18, which contains 5 to 50 w/v % of resveratrol 3-O-α-glucoside.

Advantageous Effects of Invention

The anti-skin aging agent of the present invention has excellent effects such as melanogenesis suppression, hyaluronidase inhibition, anti-oxidization, cell activation, sirtuin gene activation promotion, matrix metalloproteinase suppression, and anti-inflammation, and can effectively prevent skin aging such as sunburns, spots, dullness, reduced skin elasticity or firmness, wrinkles, sags, and skin roughness.

Moreover, resveratrol 3-O-α-glucoside as the active ingredient of the anti-skin aging agent of the present invention has high water solubility, and thus, resveratrol 3-O-α-glucoside can be incorporated at a high content, regardless of the type or form of the product. The anti-skin aging agent of the present invention can therefore impart an anti-skin aging function to various products such as cosmetics, foods, and medicines. Further, resveratrol 3-O-α-glucoside exhibits excellent stability and reduced browning with time, and thus, a product containing the anti-skin aging agent of the invention can maintain its effects over a long term, without losing its quality such as appearance.

Further, the concentrate of the present invention is obtained by concentrating resveratrol 3-O-α-glucoside in a dissolved state to a high concentration, and even when added in a small amount into various products such as cosmetics, foods, and medicines, the concentrate of the invention can be incorporated in an amount effective for expression of the anti-skin aging function. The concentrate of the present invention is therefore usable as a raw material to be added to various products into which resveratrol 3-O-α-glucoside is to be incorporated.

BRIEF DESCRIPTION OF DRAWINGS

FIG. 1 is a diagram showing the results of measuring concentrations of resveratrol metabolites in plasma (converted resveratrol concentrations in plasma) with time after oral ingestion of resveratrol 3-O-α-glucoside or resveratrol 3-O-β-glucoside in Test Example 17.

DESCRIPTION OF EMBODIMENTS

1. Anti-Skin Aging Agent

The anti-skin aging agent of the present invention contains resveratrol 3-O-α-glucoside as an active ingredient. The anti-skin aging agent of the present invention will be hereinafter described in detail.

[Active Ingredient]

Resveratrol 3-O-α-glucoside used as the active ingredient is a resveratrol derivative in which the hydroxyl group portion at the 3-position of resveratrol is bound to the hydroxyl group portion at the 1-position of α-glucose (α-pyranose) via a glucoside bond.

While the glucose forming resveratrol 3-O-α-glucoside may be either D- or L-glucose, D-glucose may be preferred. While resveratrol forming resveratrol 3-O-α-glucoside may be either cis- or trans-resveratrol, trans-resveratrol may be preferred.

Resveratrol 3-O-α-glucoside used in the anti-skin aging agent of the present invention may be either a purified product or a partially purified product.

Resveratrol 3-O-α-glucoside used in the present invention can be obtained using a known production method such as an enzymatic method or an organic synthesis method.

For example, resveratrol 3-O-α-glucoside may be produced using an enzymatic method in which sucrose phosphorylase and glucoamylase are added in the presence of resveratrol and sucrose, and the enzymatic reactions are performed.

In the above-described production method, sucrose phosphorylase and glucoamylase may be added simultaneously;

preferably, however, sucrose phosphorylase is added and reacted, and subsequently, glucoamylase is added and reacted.

Sucrose phosphorylase used in the above-described production method may be derived from, for example, *Streptococus mutans*, *Leuconostoc mesenteroides*, *Lactobacillus acidophilus*, *Bifidobacterium adolescentis*, and *Pseudomonas saccharophila*, without being limited thereto.

Glucoamylase used in the above-described production method may be derived from, for example, *Aspergillus niger*, *Rhizopus niveus*, and *Rhizopus delemar*, without being limited thereto.

In the above-described production method, resveratrol used as the raw material is poorly soluble in water, and thus, the enzymatic reactions are preferably performed in a mixture of water and an organic solvent such as dimethyl sulfoxide, dimethylformamide, isopropyl alcohol, sec-butyl alcohol, acetonitrile, or ethanol.

[Use]

The anti-skin aging agent of the present invention is used to prevent skin aging due to aging or an external stress such as UV exposure.

Specifically, resveratrol 3-O-α-glucoside has a melanogenesis suppressing effect, and can suppress pigmentation such as sunburns, spots, or dullness, and thus, the anti-skin aging agent of the present invention can be used as a melanogenesis inhibitor or a whitening agent. Resveratrol 3-O-α-glucoside also has an anti-oxidant effect, and thus, the anti-skin aging agent of the present invention can be used as an oxidative stress-reducing agent in skin tissue, in addition to suppressing pigmentation as described above.

Resveratrol 3-O-α-glucoside also has a hyaluronidase inhibitory effect or a matrix metalloproteinase expression-suppressing effect, and thus, can suppress degradation of hyaluronic acid, collagen, or the like present in the dermis layer. Further, resveratrol 3-O-α-glucoside has a cell activation effect, an effect of promoting the expression of the sirtuin genes, also referred to as the anti-aging genes, and an effect of suppressing inflammation, known as a factor in accelerating aging, and thus, can effectively suppress erythema, decreased function of skin cells due to aging, or skin aging. The anti-skin aging agent of the present invention can therefore be also used for the purpose of suppressing reduced skin elasticity or firmness, wrinkles, sags, and skin roughness, as a hyaluronidase inhibitor, a matrix metalloproteinase expression inhibitor, a cell activator, a sirtuin gene expression promoter, or an anti-inflammatory agent. It is also known that suppression of hyaluronic acid degradation in skin leads to the expression of an anti-inflammatory effect and an anti-allergic effect. Resveratrol 3-O-α-glucoside has been found to have an anti-inflammatory effect, along with the hyaluronidase inhibitory effect, and thus, can also be used for the purpose of preventing or treating a skin inflammatory disease such as atopic dermatitis, or for the purpose of maintaining a healthy skin condition.

The mode of application of the anti-skin aging agent of the present invention to the body is not limited, and any mode of application such as percutaneous application, transmucosal application, oral application, enteral application, transvenous application, transarterial application, subcutaneous application, or intramuscular application may be used. From the viewpoint of expressing the anti-skin aging effects more effectively, percutaneous application, transmucosal application, or oral application may be preferred, and percutaneous application may be more preferred.

The dose of the anti-skin aging agent of the present invention may be set as appropriate, depending on the type, use, expected effects, mode of application, and the like of the product used. In the case of percutaneous application, for example, the daily amount of resveratrol 3-O-α-glucoside applied to skin (per $cm^2$) may be set to approximately 0.5 to 100 μ. In the case of oral application, the daily amount of ingestion or administration of resveratrol 3-O-α-glucoside for an adult may be set to approximately 1 to 2000 mg.

The anti-skin aging agent of the present invention is used by being incorporated into a product required to have the anti-skin aging function. The form of the product into which the anti-skin aging agent of the present invention is incorporated may be any of solid, semi-solid, liquid, and the like, and may be set as appropriate depending on the type or use of the product.

The product into which the anti-skin aging agent of the present invention is incorporated is not limited as long as it is required to have the anti-skin aging function. Resveratrol 3-O-α-glucoside exhibits excellent absorption properties when used either percutaneously or orally, and thus, the product into which the anti-skin aging agent of the present invention is incorporated may be any of an external preparation for skin, a preparation for oral cavity, a food or beverage product, and a pharmaceutical for systemic administration (including a quasi drug for oral administration), for example. Among the above, an external preparation for skin may be preferred. The product into which the anti-skin aging agent of the present invention is incorporated will be hereinafter described.

(External Preparation for Skin)

The external preparation for skin containing the anti-skin aging agent of the present invention is provided as an external preparation for skin for skin aging prevention.

Types of external preparations for skin include, but are not limited to, cosmetics, skin cleansers, hair cleansers, deodorants, pharmaceuticals for external use (including quasi drugs for external use), and bath agents. Specific examples of cosmetics include basic skin care products such as creams, emulsions, toners, essences, ointments, oils, packs, lotions, and gels; and makeup cosmetics such as foundations, eyeshadow, lipstick, and blush. Specific examples of skin cleansers include soaps, body soaps, facial washes, cleansing creams, cleansing lotions, and cleansing milks. Specific examples of hair cleansers include shampoos, conditioners, treatments, and hair tonics. Specific examples of deodorants include antiperspirants and body odor inhibitors. Examples of pharmaceuticals for external use include hair restorers, lip creams, patches, ointments, creams, aerosols, and sprays. The dosage form of the external preparation for skin is not limited as long as it can be applied to the skin or mucous membrane, and may be set as appropriate depending on the type of the external preparation for skin. Examples of such dosage forms include ointments, creams, thickening gels, lotions, water-in-oil emulsions, oil-in-water emulsions, solids, sheets, powders, gels, mousses, sprays, and a form in which a base material such as a cloth is impregnated with the external preparation for skin.

The external preparation for skin is prepared by combining the anti-skin aging agent of the present invention with pharmacologically or cosmetically acceptable carriers or additives, and preparing the mixture into a desired dosage form. As the pharmacologically or cosmetically acceptable carriers or additives, known carriers or additives that are employed in external preparations for skin may be used. Specific examples of such carriers or additives include aqueous bases such as water and alcohols; oily bases; cooling agents, pH adjusters, thickeners, antioxidants, metal sequestrants, surfactants, emulsifiers, solubilizers, solubilizing aids, colorants (dyes and pigments), perfumes, and preservatives. Among these carriers or additives, the below-described monohydric to tetrahydric alcohols with 1 to 6 carbon atoms have the effect of further improving the solubility of resveratrol 3-O-α-glucoside, and thus, the external preparation for skin preferably contains a monohydric to tetrahydric alcohol with 1 to 6 carbon atoms. While the content of the monohydric to tetrahydric alcohol with 1 to 6 carbon atoms in the external preparation for skin is not limited, it may be 0.01 to 30 wt %, for example, preferably 1 to 20 wt %, and more preferably 5 to 20 wt %.

The external preparation for skin may optionally contain various pharmacological components for use in external preparations for skin. Examples of such pharmacological components include moisturizers, antioxidants, cell activators, whitening agents, UV inhibitors, active oxygen removing agents, blood circulation accelerators, anti-inflammatory agents, antihistamines, vitamins, plant extracts, skin astringents, skin function-enhancing agents, disinfectants, and anti-microbial agents. Types of each of these pharmacological components include, but are not limited to, the following components.

Examples of moisturizers include glycerol, 1,3-butylene glycol, proteins or their derivatives or hydrolyzates, as well as their salts (collagen, elastin, keratin, etc.), mucopolysaccharides and their derivatives (hyaluronic acid, hydrolyzed hyaluronic acid, chondroitin sulfate, etc.), amino acids and their derivatives (histidine, serine, glycine, theanine, aspartic acid, arginine, lysine, pyrrolidone carboxylic acid, N-methyl-L-serine, etc.), saccharides (sorbitol, erythritol, trehalose, inositol, glucose, xylitol, N-acetyl glucosamine, raffinose, sucrose and its derivatives, dextrin and its derivatives, honey, etc.), phosphorylated oligosaccharides and their mineral salts, D-panthenol and its derivatives, glycolipids, ceramides, glycosyl ceramides, sweet Hydrangea leaf extract, almond extract, angelica extract, avocado extract, *Althaea officinalis* extract, *Arnica* extract, hot spring water, Citrus *unshiu* peel extract, aloe extract, *Malva sylvestris* extract, *Scutellaria baicalensis* (scutellaria root) extract, *Coptidis rhizoma* extract, St. John's wort extract, *Lamium album* extract, *Ononis* extract, chamomile extract, oats extract, glabridin, glabrene, liquiritin, isoliquiritin and licorice extracts containing the same, water-soluble and oil-soluble licorice extracts, bramble extract, yellow Himalayan raspberry extract, honeysuckle (*Lonicera japonica Thunb*) extract, quince seed (*Cydonia oblonga*) extract, *Sophora flavescens* (sophora root) extract, gardenia extract, *Sasa veitchii* extract, water-soluble chlorophyll, maple leaf extract, Citrus junos extract, grapefruit extract, watercress extract, *Gentiana* (*Gentiana scabra*) extract, geranium herb extract, burdock extract, sesame extract, wheat extract, wheat germ extract, comfrey (*Symphytum officinale*) extract, *Asiasari radix* extract, cactus extract, *Saponaria officinalis* extract, salvia (sage) extract, hawthorn extract, *Rehmannia glutinosa* extract, perilla extract, herb Robert extract, meadow sweet extract, *Paeoniae radix* extract, ginger extract, Japanese iris extract, white birch extract, mentha (peppermint, *Mentha spicata*, spearmint, etc.) extracts, *Malva* (marshmallow) extract, *Equisetum arvense* extract, *Cnidium rhizome* extract, *Morus alba* (mulberry bark) extract, *Thymus vulgaris* (thyme) extract, camellia extract, *Angelica acutiloba* extract, plant worm extract, corn extract, *Houttuynia cordata* extract, hibiscus extract, white willow extract, *Potentilla tormentilla* extract, parsley extract, Job's tears (coix seed) extract, *Hamamelis virginiana* (witch-hazel) extract, rose extract, cypress extract, sunflower extract, *Tussilago farfata* extract, butcher's broom extract, grape extract, prune (Japanese plum) extract, sponge gourd extract, avocado extract, okra extract, linden extract, *Alpinia speciosa* leaf extract, *Paeonia suffruticosa* (moutan bark) extract, hop extract, jojoba leaf extract, jojoba oil, macadamia nut oil, olive oil, apricot-kernel oil, persic oil, safflower oil, sunflower seed oil, avocado oil, camellia oil, almond oil, perilla oil, sesame oil, borage (*Borago officinalis*) oil, cacao butter, shea butter, pine extract, horse chestnut extract, *Sapindus mukorossi* extract, mucin, *Lithospermum erythrorhizon* (*Lithospermi Radix*) extract, meadowfoam oil, Melissa extract, cornflower extract, *Saxifraga stolonifera* extract, lily extract, lime extract, lavender extract, apple extract, *Gentiana scabra* (*Gentianae scabrae radix*) extract, phospholipids (from soybean, egg yolk, etc.), milk vetch extract, *Sanguisorba officinalis* extract, tea (oolong tea, green tea, black tea, etc.) extracts, *Akebia* stem extract, urea, *Siraitia grosvenorii* extract, white fungus polysaccharide, seaweed extracts (brown algae such as *Laminariaceae Bory*, *Saccharina japonica*, *Undaria pinnatifida*, *Sargassum fusiforme*, *Fucus vesiculosus*, *Costaria costata*, *Saccharina gyrata*, *Ecklonia cava*, *Ecklonia stolonifera*, *Alaria crassifolia Kjellman*, *Sargassum fukvellum*, and giant kelp); red algae such as Ceylon moss, *Kappaphycus striatum*, *Eucheuma denticulatum*, *Chondrus ocellatus Holmes*, *Chondracanthus tenellus*, *Nithophyllum*, *Pyropia tenera*, *Polyopes affinis*, *Grateloupia crispata*, *Gloiopeltis tenax*, *Gracilaria vermiculophylla*, *Ceratodictyon spongiosum*, *Ceramium kondoi*, and *Campylaephora hypnaeoides*; green algae such as chlorella, green laver, *Dunaliella Chlorococcales*, *Ulva pertusa*, *Prasiola japonica*, *Aegagropila linnaei*, *Cladophoraceae*, *Acetabularia ryukyuensis*, *Chaetomorpha crassa*, *Chaetomorpha moniligera*, *Monostroma nitidum*, and *Spirogyra*; blue green algae such as spirulina), plant fermented liquids such as pear juice fermented liquid, hibiscus fermented liquid, and rice fermented liquid.

Examples of antioxidants include vitamin E and its derivatives (tocopherols and their derivatives such as dl-α (β, γ)-tocopherol, dl-α-tocopherol acetate, dl-α-tocopherol nicotinate, dl-α-tocopherol linoleate, and dl-α-tocopherol succinate, ubiquinones, etc.), vitamin A and its derivatives (retinol and its derivatives such as retinol palmitate and retinol acetate, retinal and its derivatives such as dehydroretinal, etc.), carotenoids (carotene, lycopene, astaxanthin, capsanthin, etc.), vitamin B and its derivatives (thiamine hydrochloride, thiamine sulfate, riboflavin, riboflavin acetate, pyridoxine hydrochloride, pyridoxine dioctanoate, flavin adenine nucleotide, cyanocobalamine, folic acids, nicotinamide, benzyl nicotinate and other nicotinic acids, cholines, etc.), vitamin C and its derivatives (L-ascorbic acid phosphate, L-ascorbic acid sulfate, thioctic acid, L-ascorbyl dipalmitate, L-ascorbyl tetraisopalmitate, ascorbyl glucoside, etc.), vitamin D and its derivatives (ergocalciferol, cholecalciferol, dihydroxystanal, etc.), mevalonolactone, rutin and its derivatives, thiotaurine, taurine, hydroquinone and its derivatives (arbutin and α-arbutin), histidine, catechin and its derivatives, glabridin, glabrene, liquiritin, isoliquiritin and licorice extracts containing the same, glutathione and its derivatives, gallic acid and its derivatives, Pycnogenol, bitter orange peel extract, *Oenothera biennis* extract, cucumber extract, *Millettia reticulata* extract, *Gentiana* (*Gentiana scabra*) extract, geranium herb extract, cholesterol and its derivatives, hawthorn extract, *Paeoniae radix* extract, superoxide dismutase, *Ginkgo biloba* extract, *Scutellaria baicalensis* (*scutellaria* root) extract, ginseng extract, *Rosa maikwai H. Hara* flower (*Rosa maikwai H. Hara, Rosa rugosa*) extract, *Cassia Mimosoides* (*Chamaecrista nomame*) extract, *Potentilla tormentilla* extract, parsley extract, grape extract, *Paeonia suffruticosa* (moutan bark) extract, mannitol, *Chaenomeles sinensis* (Japanese quince) extract, Melissa extract, *Alnus firma* fruit (*Alnus firma*) extract, *Saxifraga* stolonifera extract, rosemary (*Rosmarinus officinalis*) extract, bilberry extract, bilberry leaf extract, stevia extract, lettuce extract, tea extracts (oolong tea, black tea, green tea, etc.), microorganism fermentation metabolites, seaweed extract, *Ganoderma lucidum* extract, eggshell membrane extract, placenta extract, and *Siraitia grosvenorii* extract.

Examples of cell activators include vitamin A and its derivatives (retinol and its derivatives such as retinol palmitate and retinol acetate; retinal and its derivatives such as dehydroretinal, etc.), vitamin C and its derivatives (L-ascorbic acid phosphate, L-ascorbic acid sulfate, L-ascorbyl dipalmitate, L-ascorbyl tetraisopalmitate, ascorbyl glucoside, etc.), vitamin B and its derivatives (thiamine hydrochloride, thiamine sulfate, riboflavin, riboflavin acetate, pyridoxine hydrochloride, pyridoxine dioctanoate, flavin adenine nucleotide, cyanocobalamine, diisopropylamine dichloroacetate, folic acids, nicotinamide, benzyl nicotinate and other nicotinic acids, cholines, etc.), coenzyme Q10, ribonucleic acid and its salts, deoxyribonucleic acid and its salts, α- and γ-linolenic acids, xanthin and its derivatives (caffeine, etc.), almond extract, asparagus extract, amino acids and their derivatives (serine, glutamic acid, theanine, hydroxyproline, pyrrolidone carboxylic acid, γ-aminobutyric acid, γ-amino-β-hydroxybutyric acid, etc.), apricot (apricot kernel) extract, *Lupinus* extract, *Ginkgo biloba* extract, docosahexaenoic acid and its derivatives, eicosapentaenoic acid and its derivatives, *Phellodendron* (*Phellodendron* bark) extract, barley (malt) extract, kiwi extract, cucumber extract, citric acid, succinic acid, malic acid, shiitake mushroom extract, *Equisetum arvense* extract, *Swertia* herb extract, soybean extract, jujube (*Ziziphus jujuba*) extract, *Centella* extract, red pepper extract, *Calendula officinalis* extract, wheat germ extract, tomato extract, garlic extract, ginseng extract, hinokitiol, *Poria Sclerotium* extract, grape seed oil, beech extract, star fruit extract, peach extract, eucalyptus extract, lily extract, orchid extract, lettuce extract, lemon extract, rosemary (*Rosmarinus officinalis*) extract, malt root extract, animal-derived extracts (mollusk extract such as squid ink, sea shell extract, shell meat extract, pearl protein extract, fish meat extract, crista galli extract, royal jelly, silk protein and its degradation product, placenta extract, and deproteinized serum extract), lactoferrin or its degradation product or the like, microorganism-derived extract (yeast extract), microorganism fermented liquids (from lactic acid bacteria, *Lactobacillus bifidus*, etc.), and *Ganoderma lucidum* extract.

Examples of whitening agents include vitamin C and its derivatives (L-ascorbic acid phosphate, L-ascorbic acid sulfate, L-ascorbyl dipalmitate, L-ascorbyl tetraisopalmitate, ascorbyl glucoside, etc.), placenta extract, dipotassium glycyrrhizate, glabridin, glabrene, liquiritin, isoliquiritin and licorice extracts containing the same, coix seed (Job's tears) extract, *Scutellaria baicalensis* (*scutellaria* root) extract, seaweed extracts (brown algae such as *Laminariaceae Bory, Saccharina japonica, Undaria pinnatifida, Sargassum fustforme, Fucus vesiculosus, Costaria costata, Saccharina gyrata, Ecklonia cava, Ecklonia stolomfera, Alaria crassifolia Kjellman, Sargassum fulvellum*, and giant kelp); red algae such as Ceylon moss, *Chondrus ocellatus Holmes, Chondracanthus tenellus, Nithophyllum, Pyropia tenera, Polyopes affinis, Grateloupia crispata, Gloiopeltis tenax, Gracilaria vermiculophylla, Ceratodictyon spongiosum, Ceramium kondoi*, and *Campylaephora hypnaeoides*; green algae such as chlorella, green laver, *Dunaliella, Chlorococcales, Ulva per tusa, Prasiola japonica, Aegagropila linnaei, Cladophoraceae, Acetabularia ryukyuensis, Chaetomorpha crassa, Chaetomorpha moniligera, Monostroma nitidum*, and *Spirogyra*; blue green algae such as spirulina), *Magnolia denudata* extract, *Inula britannica Japonica* flower extract, grape extract, wheat extract, tomato extract, vitamin A and its derivatives (retinol and its derivatives such as retinol palmitate and retinol acetate; retinal and its derivatives such as dehydroretinal, etc.), carotenoids (carotene, lycopene, astaxanthin, capsanthin, etc.), agarose, oligosaccharides, neoagarobiose, hydroquinone and its derivatives (arbutin and α-arbutin), cysteine and its derivatives, asparagus extract, acerola extract, *Citrus depressa* extract, *Citrus junos* extract, *Prunus Speciosa* extract, *Polygonum bistorta* extract, *Rosa multiflora* fruit extract, *Pisum sativum* extract, *Lagerstroemia speciosa* extract, chamomile extract, *Myrciaria dubia* extract, *Millettia reticulata* extract, orange extract, bramble extract, *Pyracantha fortuneana* fruit extract, kiwi extract, *Sophora flavescens* (sophora root) extract, *Oenothera biennis* extract, coffee extract, sesame oil, perilla oil, *Eleutherococcus* root bark extract, *Eleutherococcus senticosus* extract, rice extract, *Asiasari radix* extract, hawthorn extract, *Cassia Mimosoides* (*Chamaecrista nomame*) extract, *Paeoniae radix* extract, white lily extract, *Morus alba* (mulberry bark) extract, *Angelica acutiloba* extract, beech extract, blackcurrant extract, *Impatiens balsamina* extract, hop extract, *Rosa maikwai H. Hara* flower (*Rosa maikwai H. Hara, Rosa rugosa*) extract, *Chaenomeles sinensis* (Japanese quince) extract, *Saxifraga stolonifera* extract, tea extracts (oolong tea, black tea, green tea, etc.), *Ganoderma lucidum* extract, microorganism fermentation metabolites, soybean extract, molasses extract, and *Siraitia grosvenorii* extract.

Examples of UV inhibitors include 2-ethylhexyl-paramethoxycinnamate, 4-tert-butyl-4'-methoxydibenzoylmethane, oxybenzone and its derivatives (2-hydroxy-4-methoxybenzophenone, 2-hydroxy-4-methoxy benzophenone-5-sulfonic acid, 2-hydroxy-4-methoxybenzophenone-5-sodium sulfonate, etc.), titanium oxide, particulate titanium oxide, zinc oxide, and barium sulfate.

Examples of active oxygen removing agents include superoxide dismutase, mannitol, quercetin, catechin and its derivatives, thiamines (thiamine hydrochloride and thiamine sulfate), riboflavins (riboflavin, riboflavin acetate, etc.), pyridoxines (pyridoxine hydrochloride, pyridoxine dioctanoate, etc.), nicotinic acids (nicotinamide, benzyl nicotinate, etc.) and other forms of vitamin B; dibutylhydroxytoluene, and butylated hydroxyanisole.

Examples of blood circulation accelerators include *Arnica* extract, red pepper tincture, *Ginkgo biloba* extract, tocopherol acetate, γ-oryzanol, nicotinic acid, tocopherol nicotinate and other nicotinic acid derivatives, and flavonoids (rutin and its glycosides, quercetin and its glycosides, hesperidin and its glycosides, hesperetin and its glycosides).

Examples of anti-inflammatory agents include glycyrrhizic acid derivatives, allantoin, tranexamic acid, bisabolol, turmeric rhizome extract, cucumber fruit extract, Edelweiss extract, rosemary leaf extract, sage leaf extract, *scutellaria* root extract, *Phellodendron* bark extract, licorice extract, *Citrus unshiu* peel extract, perilla extract, aloe extract, aloin, Aloe-emodin, flavonoids (rutin and its glycosides, quercetin and its glycosides, hesperidin and its glycosides, hesperetin and its glycosides), eucalyptus extract, and lactoferrin.

The content of the anti-skin aging agent of the present invention in the external preparation for skin may be set as appropriate, depending on the type, dosage form, and the like of the external preparation for skin. For example, the content of resveratrol 3-O-α-glucoside may be 0.001 to 2 wt %, preferably 0.01 to 2 wt %, and more preferably 0.1 to 2 wt %. In particular, when a monohydric to tetrahydric alcohol with 1 to 6 carbon atoms is contained in the external preparation for skin, resveratrol 3-O-α-glucoside can be incorporated at a high concentration, i.e., 0.05 wt % or more, and preferably 0.2 to 2.0 wt %.

(Preparation for Oral Cavity)

The preparation for oral cavity containing the anti-skin aging agent of the present invention is provided as a preparation for oral cavity for skin aging prevention.

Types of the preparation for oral cavity include, but are not limited to, dentifrices such as paste, powder, and liquid dentifrices; tooth creams; mouth rinses such as mouthwashes and gargles; pastes for oral cavity, mouth sprays, oral disintegrating films, gels, troches, tablets, and chewable tablets. The dosage form of the external preparation for skin may be set as appropriate, depending on the type.

The preparation for oral cavity is prepared by combining the anti-skin aging agent of the present invention with carriers or additives acceptable for application into the oral cavity, and preparing the mixture into a desired dosage form. Specific examples of such carriers or additives include aqueous bases such as water and alcohols; oily bases; abrasives, excipients, coating agents, binders, extenders, disintegrators, lubricants, cooling agents, pH adjusters, thickeners, antioxidants, metal sequestrants, surfactants, emulsifiers, solubilizers, solubilizing aids, colorants (dyes and pigments), flavors, and preservatives. Among these carriers or additives, the below-described monohydric to tetrahydric alcohols with 1 to 6 carbon atoms have the effect of further improving the solubility of resveratrol 3-O-α-glucoside, and thus, the preparation for oral cavity preferably contains a monohydric to tetrahydric alcohol with 1 to 6 carbon atoms. While the content of the monohydric to tetrahydric alcohol with 1 to 6 carbon atoms in the preparation for oral cavity is not limited, it may be 0.01 to 99 wt %, for example, preferably 1 to 50 wt %, and more preferably 5 to 30 wt %.

The preparation for oral cavity may optionally contain various pharmacological components for use in preparations for oral cavity. Examples of such pharmacological components include cariostatic agents, moisturizers, antioxidants, cell activators, whitening agents, active oxygen removing agents, blood circulation accelerators, anti-inflammatory agents, antihistamines, vitamins, plant extracts, skin astringents, cell activators, skin function-enhancing agents, disinfectants, and anti-microbial agents. Although types of each of these pharmacological components are not limited, specific examples of moisturizers, antioxidants, cell activators, whitening agents, active oxygen removing agents, blood circulation accelerators, and anti-inflammatory agents, for example, are the same as those incorporated into the external preparation for skin described above.

The content of the anti-skin aging agent of the present invention in the preparation for oral cavity may be set as appropriate, depending on the type, dosage form, and the like of the preparation for oral cavity. For example, the content of resveratrol 3-O-α-glucoside may be 0.001 to 2 wt %, preferably 0.01 to 2 wt %, and more preferably 0.1 to 2 wt %. In particular, when a monohydric to tetrahydric alcohol with 1 to 6 carbon atoms is contained in the preparation for oral cavity, resveratrol 3-O-α-glucoside can be incorporated at a high concentration, i.e., 0.05 wt % or more, and preferably 0.2 to 2 wt %, which cannot be achieved with resveratrol or its β-glycoside.

(Food or Beverage Product)

The food or beverage product containing the anti-skin aging agent of the present invention is provided as a food or beverage product having the anti-skin aging function. The food or beverage product containing the anti-skin aging agent of the present invention can be provided not only as a general food or beverage product, but also as a food for specified health uses, a nutritional supplement, a functional food, a food for invalids, or the like.

Types of the food or beverage product include, but are not limited to, frozen desserts such as ice creams, iced milk, and sherbets; dairy products such as milk, yogurt, ice creams, butter, margarine, cheese, and whipped cream; Western confectionery, Japanese confectionery, snacks, and the like, specifically, sweets such as red bean paste (anko), sweet jellied red bean paste (yokan), steamed filled dumplings, chocolates, gums, jellies, gummies, agar, Chinese almond jelly, cakes, kasutera (Japanese sponge cake), cookies, rice crackers, and tablet candy; bread; rice cakes; seafood paste products such as boiled fish pastes and fishcake tubes; processed meat products such as sausages and hams; processed fruit products such as jams, marmalade, and fruit sauces; seasonings such as Japanese sweetened sake (mirin), cooking liquor, dressings, mayonnaise, and miso paste; noodles such as udon noodles (Japanese noodles made of wheat flour) and buckwheat noodles; pickles; bottled and canned products such as meat, fish meat, and fruits; capsules such as soft capsules and hard capsules; nutritional drinks, carbonated beverages such as soda and pop, soft beverages, medicinal beverages, alcoholic beverages, powdered juices, and other beverages. Resveratrol 3-O-α-glucoside shows extremely good solubility in a mixture of ethanol and water. Thus, in view of this characteristic, a suitable example of the food or beverage product into which the anti-aging agent of the present invention is incorporated may be an alcoholic beverage. As used herein, the term "alcoholic beverage" encompasses alcoholic drinks such as beer, Japanese clear distilled liquor (shochu), wine, whiskey, Japanese sake, spirits, and liqueur, as well as nutritional drinks containing ethanol. While the ethanol content in an alcoholic beverage is not limited, it may be 0.001 to 25 wt %, for example, preferably 0.001 to 20 wt %, and more preferably 0.001 to 15 wt %.

The food or beverage product can be prepared by combining the anti-skin aging agent of the present invention with other food materials and additive components, preparing the mixture into a desired dosage form, and processing or cooking the resulting product in accordance with the type of the food or beverage product.

The content of the anti-skin aging agent of the present invention in the food or beverage product may be set as appropriate, depending on the type, dosage form, and the like of the food or beverage product. For example, the content of resveratrol 3-O-α-glucoside may be 0.001 to 90 wt %, preferably 0.01 to 50 wt %, and more preferably 0.1 to 30 wt %. More specifically, when the anti-skin aging agent of the present invention is incorporated into an alcoholic beverage, the content of the anti-skin aging agent in the alcoholic beverage may be 0.001 to 5 wt %, for example, preferably 0.01 to 5 wt %, more preferably 0.05 to 5 wt %, and particularly preferably 0.12 to 5 wt %.

Further, when the anti-skin aging agent of the present invention is used in the field of food and beverage products, the anti-skin aging agent of the present invention, either alone or in combination with other components, can be provided as an additive for a food or beverage product for skin aging prevention. When the anti-skin aging agent of the present invention is used as a food additive, the content of resveratrol 3-O-α-glucoside in the food additive, the amount of the food additive added to the food or beverage product, and the like may be set as appropriate to satisfy the above-described content of resveratrol 3-O-α-glucoside in the food or beverage product to which the food additive is added.

(Pharmaceutical for Systemic Administration)

The pharmaceutical for systemic administration containing the anti-skin aging agent of the present invention (including quasi drugs for oral administration) is provided as a pharmaceutical for skin aging prevention.

While the mode of administration of the pharmaceutical for systemic administration is not limited as long as it is systemic administration, it may be oral administration, enteral administration, transvenous administration, transarterial administration, subcutaneous administration, or intramuscular administration, for example. Among these types of systemic administration, oral administration may be preferred.

The dosage form of the pharmaceutical for systemic administration is not limited, and may be set as appropriate depending on the mode of administration. Examples of dosage forms include powders, granules, tablets, capsules, pills, and liquids. Among these dosage forms, liquids such as nutritional drinks may be preferred.

The pharmaceutical for systemic administration is prepared by combining the anti-skin aging agent of the present invention with pharmacologically acceptable carriers or additives, and preparing the mixture into a desired dosage form. Specific examples of such carriers or additives include aqueous bases such as water and alcohols; oily bases; abrasives, excipients, coating agents, binders, extenders, disintegrators, lubricants, cooling agents, pH adjusters, thickeners, antioxidants, metal sequestrants, surfactants, emulsifiers, solubilizers, solubilizing aids, colorants (colors and pigments), perfumes, and preservatives. Among these carriers or additives, the below-described monohydric to tetrahydric alcohols with 1 to 6 carbon atoms have the effect of further improving the solubility of resveratrol 3-O-α-glucoside. Thus, when the pharmaceutical for systemic administration is in the form of a liquid, it preferably contains a monohydric to tetrahydric alcohol with 1 to 6 carbon atoms. While the content of the monohydric to tetrahydric alcohol with 1 to 6 carbon atoms in the pharmaceutical is not limited, it may be 0.001 to 75 wt %, for example, preferably 0.001 to 50 wt %, and more preferably 0.001 to 15 wt %.

The pharmaceutical for systemic administration may optionally contain various pharmacological components for use in pharmaceuticals for systemic administration. Examples of such pharmacological components include moisturizers, antioxidants, cell activators, whitening agents, active oxygen removing agents, blood circulation accelerators, anti-inflammatory agents, antihistamines, vitamins, plant extracts, blood circulation accelerators, skin function-enhancing agents, disinfectants, and anti-microbial agents. Although types of each of these pharmacological components are not limited, specific examples of moisturizers, antioxidants, cell activators, whitening agents, active oxygen removing agents, blood circulation accelerators, and anti-inflammatory agents, for example, are the same as those incorporated into the external preparation for skin described above.

The content of the anti-skin aging agent of the present invention in the pharmaceutical for systemic administration may be set as appropriate, depending on the type, dosage form, and the like of the pharmaceutical for systemic administration. For example, the content of resveratrol 3-O-α-glucoside may be 0.05 to 100 wt %, preferably 0.1 to 90 wt %, and more preferably 0.2 to 50 wt %. In particular, when the pharmaceutical is in the form of a liquid containing a monohydric to tetrahydric alcohol with 1 to 6 carbon atoms, resveratrol 3-O-α-glucoside can be incorporated at a high concentration, i.e., 0.05 wt % or more, and preferably 0.12 to 5 wt %.

2. Concentrate

In the concentrate of the present invention, resveratrol 3-O-α-glucoside is contained in a solvent containing a monohydric to tetrahydric alcohol with 1 to 6 carbon atoms. When resveratrol 3-O-α-glucoside and the solvent containing a monohydric to tetrahydric alcohol with 1 to 6 carbon atoms are present together, resveratrol 3-O-α-glucoside in a dissolved state can be concentrated to a high concentration.

Resveratrol 3-O-α-glucoside used in the concentrate of the present invention is as described in "1. Anti-Skin Aging Agent" above. The content of resveratrol 3-O-α-glucoside in the concentrate of the present invention varies depending on the type, amount, and the like of the monohydric to tetrahydric alcohol with 1 to 6 carbon atoms used. For example, the content may be 5 to 50 w/v %, preferably 8 to 40 w/v %, and more preferably 10 to 30 w/v %.

In the concentrate of the present invention, the monohydric to tetrahydric alcohol with 1 to 6 carbon atoms functions as a solvent for dissolving resveratrol 3-O-α-glucoside. The monohydric to tetrahydric alcohol with 1 to 6 carbon atoms is not limited in type, and may be selected from pharmacologically or cosmetically acceptable ones, or edible ones, depending on the use of the concentrate of the present invention.

Specific examples of monohydric alcohols with 2 to 6 carbon atoms include ethanol; propanols such as 1-propanol and 2-propanol; butanols such as 1-butanol, 2-methyl-2-propanol, 2-methyl-1-propanol, and 2-butanol; pentanols such as 1-pentanol, 2-pentanol, 3-pentanol, isoamyl alcohol, tert-amyl alcohol, and neopentyl alcohol; hexanols such as 1-hexanol, 2-hexanol, 3-hexanol, 2-methyl-1-pentanol, 3-methyl-1-pentanol, and 4-methyl-1-pentanol.

Specific examples of dihydric alcohols with 2 to 6 carbon atoms include ethylene glycol, propylene glycol (1,2-propanediol), trimethylene glycol, 1,3-butylene glycol, 1,2-pentanediol, 1,2-hexanediol, diethylene glycol, and dipropylene glycol.

An example of a trihydric alcohol with 2 to 6 carbon atoms may be glycerol.

An example of a tetrahydric alcohol with 2 to 6 carbon atoms may be diglycerol.

Among these monohydric to tetrahydric alcohols with 1 to 6 carbon atoms, preferred are a monohydric alcohol with 2 to 3 carbon atoms, a dihydric alcohol with 4 to 6 carbon atoms, and a trihydric alcohol with 3 to 4 carbon atoms; and more preferred are ethanol, propylene glycol, 1,3-butylene glycol, dipropylene glycol, 1,2-pentanediol, 1,2-hexanediol, and glycerol, from the viewpoint of improving the solubility of resveratrol 3-O-α-glucoside to allow resveratrol 3-O-α-glucoside to be concentrated to an even higher concentration.

These monohydric to tetrahydric alcohols with 1 to 6 carbon atoms may be used alone or in combination of two or more.

In the concentrate of the present invention, the solvent may be composed of a monohydric to tetrahydric alcohol with 1 to 6 carbon atoms alone, or may also contain an aqueous solvent (for example, water) other than the monohydric to tetrahydric alcohol with 1 to 6 carbon atoms. In the concentrate of the present invention, the higher is the content of the aqueous solvent other than the monohydric to tetrahydric alcohol with 1 to 6 carbon atoms, the lower is the solubility of resveratrol 3-O-α-glucoside. Thus, the content of the aqueous solvent other than the monohydric to tetrahydric alcohol with 1 to 6 carbon atoms is set as appropriate, depending on the amount of resveratrol 3-O-α-glucoside to be dissolved, the type of the monohydric to tetrahydric alcohol with 1 to 6 carbon atoms, and the like. For example, the amount of resveratrol 3-O-α-glucoside may be set as appropriate in the range of 5 to 100 parts by weight, preferably 25 to 100 parts by weight, and more preferably 50 to 100 parts by weight, based on a total amount of 100 parts by weight of the solvents (total amount of the monohydric to tetrahydric alcohol with 1 to 6 carbon atoms and the other aqueous solvent) contained in the concentrate of the present invention. More specifically, the following are exemplary ranges of proportions of the monohydric to tetrahydric alcohol with 1 to 6 carbon atoms, per total amount of the solvents contained in the concentrate of the present invention.

Where ethanol is used as the monohydric to tetrahydric alcohol with 1 to 6 carbon atoms: 25 to 100 parts by weight, preferably 50 to 100 parts by weight, and more preferably 75 to 100 parts by weight of ethanol, per total amount of 100 parts by weight of the solvents.

Where propylene glycol is used as the monohydric to tetrahydric alcohol with 1 to 6 carbon atoms: 50 to 100 parts by weight, preferably 75 to 100 parts by weight, and more preferably 90 to 100 parts by weight of propylene glycol, per total amount of 100 parts by weight of the solvents.

Where 1,3-butylene glycol is used as the monohydric to tetrahydric alcohol with 1 to 6 carbon atoms: 25 to 100 parts by weight, preferably 50 to 100 parts by weight, and more preferably 75 to 100 parts by weight of 1,3-butylene glycol, per total amount of 100 parts by weight of the solvents.

Where dipropylene glycol is used as the monohydric to tetrahydric alcohol with 1 to 6 carbon atoms: 25 to 100 parts by weight, preferably 50 to 100 parts by weight, and more preferably 75 to 100 parts by weight of dipropylene glycol, per total amount of 100 parts by weight of the solvents.

Where 1,2-pentanediol is used as the monohydric to tetrahydric alcohol with 1 to 6 carbon atoms: 25 to 100 parts by weight, preferably 50 to 100 parts by weight, and more preferably 75 to 100 parts by weight of 1,2-pentanediol, per total amount of 100 parts by weight of the solvents.

Where 1,2-hexanediol is used as the monohydric to tetrahydric alcohol with 1 to 6 carbon atoms: 10 to 100 parts by weight, preferably 25 to 100 parts by weight, and more preferably 50 to 100 parts by weight of 1,2-hexanediol, per total amount of 100 parts by weight of the solvents.

Where glycerol is used as the monohydric to tetrahydric alcohol with 1 to 6 carbon atoms: 75 to 100 parts by weight, preferably 90 to 100 parts by weight, and more preferably 95 to 100 parts by weight of glycerol, per total amount of 100 parts by weight of the solvents.

The concentrate of the present invention may further optionally contain additives such as a thickener, an antioxidant, a metal sequestrant, a surfactant, an emulsifier, a colorant (a color or pigment), a perfume, and a preservative, in a range that does not impair the effects of the invention.

The concentrate of the present invention is used as an additive for manufacturing a product such as the external preparation for skin, the preparation for oral cavity, the food or beverage product, or the pharmaceutical for systemic administration. The concentrate of the present invention contains a high concentration of resveratrol 3-O-α-glucoside in a dissolved state, and thus, when added only in a small amount to the above-described product, the concentrate can provide the product with the functionality of resveratrol 3-O-α-glucoside. The product and the like to which the concentrate of the present invention is added are as described in the "1. Anti-Skin Aging Agent" section above.

EXAMPLES

The present invention will be hereinafter described with reference to examples; however, the invention should not be construed as being limited to these examples.

Production Example 1

Production of Resveratrol 3-O-α-Glucoside

Five grams of resveratrol (Tokyo Chemical Industry Co., Ltd.) and 250 g of sucrose (Wako Pure Chemical Industries, Ltd.) were added to 500 mL of a 30 wt % aqueous solution of dimethyl sulfoxide, and dissolved with stirring at 45° C. Sucrose phosphorylase (from *Streptcoccus mutans*, 40000 units) was added to the resulting mixture, and reacted at 45° C. for 42 hours. To this reaction mixture, 250 mL of water and glucoamylase (from *Aspergillus niger*, 20 units) were further added, and further reacted for 4 hours. After the completion of the reaction, HPLC analysis of the resulting mixture under the following conditions showed the formation of approximately 480 mg of resveratrol 3-O-α-glucoside and 40 mg of resveratrol 4'-O-α-glucoside.

<HPLC Analysis Conditions>
Column: LiChrospher RP-18 (5 μm)-packed LiChroCART 250-4 (Merck Ltd.)
Mobile phase: acetonitrile-0.2% aqueous solution of phosphoric acid (45:55, v:v) mixed solution
Column temperature: 40° C.
Flow rate: 0.7 mL/min
Detection wavelength: 310 nm Three liters of water were added to the obtained enzyme reaction mixture, the precipitate formed was removed by filtering, and then the filtrate was loaded into the Amberlite XAD4 column previously equilibrated with water. The adsorbed fraction was eluted by stepwise elution using ethanol/water. Then, the mixed fraction of resveratrol 3-O-α-glucoside and resveratrol 4'-O-α-glucoside was concentrated, the concentrate was loaded into the FS-1801 column (Organo Corporation) previously equilibrated with 20% acetonitrile, and eluted with the same solution, thus separating and purifying these components. Each of the purified fractions was concentrated and freeze-dried, thus giving 300 mg of resveratrol 3-O-α-glucoside powder and 30 mg of resveratrol 4'-O-α-glucoside powder. Note that resveratrol 3-O-α-glucoside used in each of the following examples was that obtained in Production Example 1.

Example 1

Evaluation of the Melanogenesis Suppressing Effect of Resveratrol 3-O-α-Glucoside (1)

Resveratrol 3-O-α-glucoside, resveratrol (Tokyo Chemical Industry Co., Ltd.), or resveratrol 3-O-β-glucoside (Tokyo Chemical Industry Co., Ltd.) was prepared into a 0.2 wt % solution or suspension with the addition of PBS, and the resulting solution or suspension was used as a test substance. A skin model (MEL-312B; MatTek) was used, and 50 μL of the test substance was added to the horny layer side of the skin model and cultured in a special medium (EPI-100NMM-113; MatTek) at 37° C. for 16 days. On days 2, 4, 7, 9, 11, and 14, the medium and the test substance were replaced with fresh ones. As a control group, the same operation was performed using PBS instead of the test substance.

After 16 days of culture, the skin model was visually observed, and the amount of melanin in the skin model was evaluated. The amount of melanin was measured using the following method. Initially, the collected skin model was subjected to enzymatic degradation by proteinase-K, and was subsequently homogenated in PBS containing 1% triton X-100. Melanin was then extracted by washing with 10% TCA and ethanol. Next, the extracted melanin was dissolved in 0.5 mL of 1N-NaOH containing 10% DMSO at 80° C. for 2 hours, and the amount of melanin was quantified by measuring absorbance at 470 nm.

The obtained results are shown in Table 1. As is clear from Table 1, resveratrol 3-O-α-glucoside exhibited a melanogenesis suppressing effect remarkably higher than those of resveratrol and resveratrol 3-O-β-glucoside. On the other hand, resveratrol 3-O-β-glucoside had a melanogenesis suppressing effect lower than that of resveratrol.

TABLE 1

|   | Visual Observation | Relative Amount of Melanin |
|---|---|---|
| PBS (Control Group) | reference | 100% |
| 0.2 wt % Resveratrol 3-O-α-Glucoside | clearly whiter than the control group | 46% |
| 0.2 wt % Resveratrol 3-O-β-Glucoside | the same as the control group | 79% |
| 0.2 wt % Resveratrol | a little whiter than the control group | 63% |

Example 2

Evaluation of the Melanogenesis Suppressing Effect of Resveratrol 3-O-α-Glucoside (2)

Resveratrol 3-O-α-glucoside was prepared into a 0.2 wt % solution, a 0.1 wt % solution, or a 0.01 wt % solution with the addition of PBS. The resulting solution was used as a test substance, and the melanogenesis suppressing effect was evaluated using the same method as that of Example 1 above.

The obtained results are shown in Table 2. These results confirmed that resveratrol 3-O-α-glucoside exhibits a melanogenesis suppressing effect in a concentration-dependent manner.

TABLE 2

|   | Visual Observation | Relative Amount of Melanin |
|---|---|---|
| PBS (Control Group) | reference | 100% |
| 0.2 wt % Resveratrol 3-O-α-Glucoside | clearly whiter than the control group | 46% |
| 0.1 wt % Resveratrol 3-O-α-Glucoside | a little whiter than the control group | 67% |
| 0.01 wt % Resveratrol 3-O-α-Glucoside | slightly whiter than the control group | 88% |

Example 3

Evaluation of the Melanogenesis Suppressing Effect of a Lotion Containing Resveratrol 3-O-α-Glucoside The amount of melanin in the skin model was measured using the same method as that of Example 1 above, except that lotions of the compositions shown in Table 3 were used as test substances, the amount of the test substances added to the horny layer side was changed to 25 μL, and the culture period was changed to 14 days.

As a result, the amount of melanin in the skin model administered the lotion of Example 3 was 64% that of the skin model administered the lotion of Comparative Example 1. The foregoing results confirmed that resveratrol 3-O-α-glucoside can exhibit a melanogenesis suppressing effect in a lotion formulation as well.

TABLE 3

| Raw Materials | Example 3 | Comparative Example 1 |
|---|---|---|
| 1,3-Butylene Glycol | 1.0 | 1.0 |
| Dipropylene Glycol | 1.0 | 1.0 |
| Glycerol | 5.0 | 5.0 |
| Methylparaben | 0.2 | 0.2 |
| Resveratrol 3-O-α-Glucoside | 0.1 | — |
| Water | balance | balance |
| Total | 100 | 100 |

In the table, the content of each ingredient is in wt %.

Example 4

Evaluation of the Melanogenesis Suppressing Effect of an Essence Containing Resveratrol 3-O-α-Glucoside The amount of melanin in the skin model was measured using the same method as that of Example 1 above, except that essences of the compositions shown in Table 4 were used as test substances, the amount of the test substances added to the horny layer side was changed to 25 μL, and the culture period was changed to 14 days.

As a result, the amount of melanin in the skin model administered the essence of Example 4 was 43% that of the skin model administered the essence of Comparative Example 2. The foregoing results confirmed that resveratrol 3-O-α-glucoside can exhibit a melanogenesis suppressing effect in an essence formulation as well.

TABLE 4

| Raw Materials | Example 4 | Comparative Example 2 |
|---|---|---|
| 1,3-Butylene Glycol | 3.0 | 3.0 |
| Dipropylene Glycol | 1.0 | 1.0 |
| Glycerol | 6.0 | 6.0 |
| 1,2-Pentanediol | 3.0 | 3.0 |
| Acrylic Acid-Alkyl Methacrylate (C10-30) Copolymer (2 wt % Solution) | 20.0 | 20.0 |
| Methylparaben | 0.2 | 0.2 |
| Resveratrol 3-O-α-Glucoside | 0.2 | — |
| 1M NaOH | adjusted to a pH of 6.5 | adjusted to a pH of 6.5 |
| Water | balance | balance |
| Total | 100 | 100 |

In the table, the content of each ingredient is in wt %.

Example 5

Evaluation of the Melanogenesis Suppressing Effect of a Cream Containing Resveratrol 3-O-α-Glucoside The amount of melanin in the skin model was measured using the same method as that of Example 1 above, except that creams of the compositions shown in Table 5 were used as test substances, the amount of the test substances added to the horny layer side was changed to 25 μL, and the culture period was changed to 14 days.

As a result, the amounts of melanin in the skin model administered the creams of Examples 5-1 and 5-2 were 61% and 62%, respectively, the amount of melanin in the skin model administered the cream of Comparative Example 3. The foregoing results confirmed that resveratrol 3-O-α-glucoside can exhibit a melanogenesis suppressing effect in a cream formulation as well.

TABLE 5

| Raw Materials | Example 5-1 | Example 5-2 | Comparative Example 3 |
|---|---|---|---|
| 1,3-Butylene Glycol | 5.0 | 5.0 | 5.0 |
| Tetraglycerol Monostearate | 1.5 | 1.5 | 1.5 |
| Hydroxypropyl Guar Gum | 0.5 | 0.5 | 0.5 |
| Methylparaben | 0.1 | 0.1 | 0.1 |
| Glycerol | 2.0 | 2.0 | 2.0 |
| 1,2-Hexanediol | 2.0 | 2.0 | 2.0 |
| Polyoxyethylene Hydrogenated Castor Oil | 1.0 | 1.0 | 1.0 |
| Glycerol Monostearate | 1.0 | 1.0 | 1.0 |
| Behenyl Alcohol | 1.0 | 1.0 | 1.0 |
| Squalane | 7.0 | 7.0 | 7.0 |
| Cyclomethicone | 6.0 | 6.0 | 6.0 |
| Triglyceryl-2-ethylhexanoate | 7.0 | 7.0 | 7.0 |
| Propylparaben | 0.1 | 0.1 | 0.1 |
| Resveratrol 3-O-α-Glucoside | 0.3 | 0.5 | — |
| Water | balance | balance | balance |
| Total | 100 | 100 | 100 |

In the table, the content of each ingredient is in wt %.

Example 6

Evaluation of the Hyaluronidase Inhibitory Effect of Resveratrol 3-O-α-Glucoside The following sample solution, enzyme solution, and hyaluronic acid solution were prepared.
(Sample Solution)
Resveratrol 3-O-α-glucoside was dissolved in a 0.2 M acetate buffer solution (pH 4.0) to a concentration of 0.025 or 0.1 wt %, and the resulting solution was used as a sample solution.
(Enzyme Solution)
In 1.5 mL of a 0.2 M acetate buffer solution (pH 4.0), 7400 units of hyaluronidase (from bovine testes; Sigma-Aldrich Co. LLC.) were dissolved, and the resulting solution was used as the enzyme solution.
(Hyaluronic Acid Solution)
In 12.5 mL of a 0.2 M acetate buffer solution (pH 4.0), 10 mg of sodium hyaluronate (from crista galli; Wako Pure Chemical Industries, Ltd.) was dissolved, and the resulting solution was used as the hyaluronic acid solution.

Using each of the solutions prepared as above, the hyaluronidase inhibitory effect was evaluated in accordance with the following procedures. One-hundred microliters of the sample solution, 50 μL of the enzyme solution, and 200 μL of the hyaluronic acid solution were mixed and reacted at 37° C. for 40 minutes. Then, 100 μL each of a 0.4 M aqueous solution of sodium hydroxide and a 1 M aqueous solution of potassium borate were added to the mixture, and the reaction was stopped. After the reaction was stopped, 3,000 μL of p-dimethylaminobenzaldehyde was added, and the mixture was heated at 37° C. for 20 minutes. The absorbance at 585 nm was subsequently measured. From the measured value of absorbance, the hyaluronidase inhibition ratio was determined in accordance with the equation shown below. As a control solution, a 0.2M acetate buffer solution (pH 4.0) was used instead of the sample solution. Moreover, as a blank for each of the solutions, a 0.2 M acetate buffer solution (pH 4.0) was added instead of the enzyme solution, and the same operation was performed.

$$\text{Hyaluronidase inhibition ratio (\%)} = \{(A-B)-(C-D)\}/(A-B) \times 100 \quad \text{[Equation 1]}$$

A: Absorbance of the reaction mixture containing the control solution
B: Absorbance of the reaction mixture (blank) containing the control solution
C: Absorbance of the reaction mixture containing the sample solution
D: Absorbance of the reaction mixture (blank) containing the sample solution The obtained results are shown in Table 6. These results confirmed that resveratrol 3-O-α-glucoside has an excellent hyaluronidase inhibitory effect.

TABLE 6

| Resveratrol 3-O-α-Glucoside Concentration (wt %) in the Sample Solution | Hyaluronidase Inhibition Ratio (%) |
|---|---|
| 0.025 | 7.6 |
| 0.1 | 20.6 |

Example 7

Evaluation of the Anti-Oxidant Effect (Radical Scavenging Effect) of Resveratrol 3-O-α-Glucoside The following sample solution and DPPH solution were prepared.
(Sample Solution)
Resveratrol 3-O-α-glucoside was dissolved in water to a concentration of 100, 250, 500, or 1000 μmol/L, and the resulting solution was used as a sample solution.
(DPPH Solution)
In 10 mL of ethanol, 2 mg of 2,2-diphenyl-1-picrylhydrazyl (Wako Pure Chemical Industries, Ltd.) was dissolved, and the resulting solution was used as the DPPH solution.

Using each of the solutions prepared as above, the DPPH radical scavenging effect was evaluated in accordance with the following procedures. One-hundred microliters of the sample solution, 500 μL, of the DPPH solution, 250 μL of a 200 μM MES (2-morpholinoethanesulfonic acid) buffer, and 150 μL of distilled water were mixed and reacted at 30° C. for 30 minutes. The absorbance at 517 nm was subsequently measured. Further, distilled water (control solution) was used instead of the sample solution, and the absorbance at 517 nm was measured under the same conditions as described above. From the measured value of absorbance, the DPPH radical scavenging ratio was determined in accordance with the equation shown below.

$$\text{DPPH radical scavenging ratio (\%)} = (A-B)/A \times 100 \quad \text{[Equation 2]}$$

A: Absorbance of the reaction mixture containing the control solution
B: Absorbance of the reaction mixture containing the sample solution The obtained results are shown in Table 7. These results confirmed that resveratrol 3-O-α-glucoside has an anti-oxidant effect based on its excellent radical scavenging effect.

TABLE 7

| Resveratrol 3-O-α-Glucoside Concentration (µmol/L) in the Sample Solution | DPPH Radical Scavenging Ratio (%) |
|---|---|
| 100 | 13 |
| 250 | 30 |
| 500 | 50 |
| 1000 | 75 |

Example 8

Evaluation of the Anti-Oxidant Effect (Superoxide Dismutase (SOD)-Like Effect) of Resveratrol 3-O-α-Glucoside The following sample solution was prepared.
(Sample Solution)

Resveratrol 3-O-α-glucoside was dissolved in a 15% ethanol solution to a concentration of 5, 10, or 20 mmol/L, and the resulting solution was used as a sample solution.

Using the sample solution prepared as above, the SOD-like activity was evaluated using an SOD measurement kit (SOD Test Wako; Wako Pure Chemical Industries, Ltd.).

The obtained results are shown in Table 8. These results confirmed that resveratrol 3-O-α-glucoside has an anti-oxidant effect based on its excellent SOD-like effect.

TABLE 8

| Resveratrol 3-O-α-Glucoside Concentration (mmol/L) in the Sample Solution | SOD-Like Activity (%) |
|---|---|
| 5 | 18 |
| 10 | 35 |
| 20 | 47 |

Example 9

Evaluation of the Skin Cell Activation Effect of Resveratrol 3-O-α-Glucoside

Using a three-dimensional human skin model, the skin cell activation effect of resveratrol 3-O-α-glucoside was investigated.

Resveratrol 3-O-α-glucoside was prepared into an aqueous solution having a concentration of 0.02, 0.05, 0.07, or 0.1 wt %, and the resulting solution was used as a sample solution. One-hundred microliters of the sample solution were administered to the horny layer side of the human skin model (EpiDerm EPI-200; MatTek), and cultured in 5 mL of a special medium (EPI-100-ASY) at 37° C. for 72 hours. After the culture, the survival rate of cells in the skin model was measured using the MTT (Thiazolyl Blue Tetrazolium Bromide) method based on the manual, and a relative ratio of the survival rate (cell growth improvement rate; %) after the administration of each of the sample solutions was calculated, taking as 100% the survival rate of a control group to which water not containing resveratrol 3-O-α-glucoside was administered.

The obtained results are shown in Table 9. As shown in Table 9, resveratrol 3-O-α-glucoside showed a significant increase in cell survival rate in a concentration-dependent manner. That is, resveratrol 3-O-α-glucoside was confirmed to have the effect of activating epidermal cells, and to be effective against skin aging.

TABLE 9

| Resveratrol 3-O-α-Glucoside Concentration (wt %) in the Sample Solution | Cell Growth Improvement Rate (%) |
|---|---|
| 0.02 | 106 |
| 0.05 | 115 |
| 0.07 | 116 |
| 0.1 | 117 |

Example 10 Evaluation of the Anti-Inflammatory Effect of Resveratrol 3-O-α-Glucoside Normal human epidermal keratinocytes were seeded into 12-well culture plates at $5 \times 10^4$ cells per well. As the medium, EpiLife KG-2 medium supplemented with insulin, the human epithelial growth factor (hEGF), hydrocortisone, anti-microbial agents, and bovine pituitary extract (BPE) was used (basal medium), and the cells were preincubated in 5% $CO_2$ at 37° C. for 48 hours. Further, the cells were incubated for additional 48 hours in a medium obtained by removing hydrocortisone only from the basal medium (assay medium). Next, the medium was replaced with an inflammation-inducing medium obtained by supplementing the assay medium with Poly I:C (double strand of inosine ribonucleotide and cytidine ribonucleotide strands) to a concentration of 1 µg/mL, and the cells were cultured for 9 hours, thus preparing an inflammation model. Next, the medium was removed, the cells were washed with PBS (Phosphate-Buffered Saline), and then the medium was replaced with a sample medium obtained by supplementing the assay medium with resveratrol 3-O-α-glucoside to a concentration of 0.001 wt %, and the cells were further cultured in 5% $CO_2$ at 37° C. for 15 hours. After the culture, total RNA was extracted from the cells, and the level of expression of the proinflammatory cytokine IL-1β gene was quantified by real time PCR. As a control group, cells were cultured without Poly I:C and resveratrol 3-O-α-glucoside, and total RNA collected from these cells was used. As a comparative group, cells in which inflammation was induced by Poly I:C were cultured without resveratrol 3-O-α-glucoside, and total RNA collected from these cells was used.

Taking as 100% the level of expression of the IL-1β gene for the control group, a relative ratio of the expression level of the IL-1β gene for each of the comparative group and the resveratrol 3-O-α-glucoside-supplemented group (IL-1β gene expression ratio, %) was calculated. In the measurement of the expression level of the IL-1β gene, PPIA (peptidylprolyl isomerase A) was used for internal standard correction.

The obtained results are shown in Table 10. As is clear from Table 10, the addition of 0.001 wt % resveratrol 3-O-α-glucoside was confirmed to provide a significant anti-inflammatory effect. It has been reported that in one mechanism of UV-induced inflammatory response in skin, an inflammatory response is induced by double-stranded RNA as a signal produced in skin cells by the action of ultraviolet radiation. Hence, resveratrol 3-O-α-glucoside was confirmed to be effective in suppressing skin aging caused by an inflammatory response or erythema occurring in skin due to the influence of ultraviolet radiation, for example.

TABLE 10

| Test Group | IL-1β Gene Expression Ratio (%) |
|---|---|
| Comparative Group | 1210 |
| Resveratrol 3-O-α-Glucoside-Supplemented Group | 885 |

Example 11

Evaluation of Reduction of Inflammation through Pretreatment with Resveratrol 3-O-α-Glucoside Normal human epidermal keratinocytes were seeded into 12-well culture plates at $5 \times 10^4$ cells per well. As the medium, EpiLife KG-2 medium (basal medium) supplemented with insulin, hEGF, hydrocortisone, anti-microbial agents, and BPE was used, and the cells were preincubated in 5% $CO_2$ at 37° C. for 48 hours. Further, the cells were incubated for additional 24 hours in a medium obtained by removing hydrocortisone only from the basal medium (assay medium). Next, the medium was replaced with a sample medium obtained by supplementing the assay medium with resveratrol 3-O-α-glucoside to a concentration of 0.001 wt %, the cells were cultured in 5% $CO_2$ at 37° C. for 24 hours, and the cultured cells were pretreated with resveratrol 3-O-α-glucoside. To the culture plates after 24 hours, Poly I:C (double strand of inosine ribonucleotide and cytidine ribonucleotide strands) was added to a concentration of 1 μg/mL, and the cells were cultured for 9 hours to induce inflammation. After the medium was removed and the cells were washed with PBS, total RNA was extracted from the cells, and the level of expression of the proinflammatory cytokine IL-1β gene was quantified by real time PCR. As a control group, cells were similarly cultured without Poly I:C and resveratrol 3-O-α-glucoside, and total RNA collected from these cells was used. As a comparative group, cells in which inflammation was similarly induced by Poly I:C were not pretreated with resveratrol 3-O-α-glucoside, and total RNA collected from these cells was used.

Taking as 100% the level of expression of the IL-1β gene for the control group, a relative ratio of the expression level of the IL-1β gene for each of the comparative group and the resveratrol 3-O-α-glucoside-supplemented group (IL-1β gene expression ratio, %) was calculated. In the measurement of the expression level of the IL-1β gene, PPIA was used for internal standard correction.

The obtained results are shown in Table 11. The results revealed that the pretreatment with 0.001 wt % resveratrol 3-O-α-glucoside can significantly reduce Poly I.C-induced inflammation. That is, these test results confirmed that resveratrol 3-O-α-glucoside is also effective in preventing skin aging caused by an inflammatory response or erythema occurring in skin due to the influence of ultraviolet radiation, for example.

TABLE 11

| Test Group | IL-1β Gene Expression Ratio (%) |
|---|---|
| Comparative Group | 871 |
| Resveratrol 3-O-α-Glucoside-Supplemented Group | 697 |

Example 12

Evaluation of the Sirtuin 1 Gene Expression-Promoting Effect of Resveratrol 3-O-α-Glucoside (1)

Normal human epidermal keratinocytes were seeded into 12-well culture plates at $7.5 \times 10^4$ cells per well. As the medium, EpiLife KG-2 medium supplemented with insulin, hEGF, hydrocortisone, anti-microbial agents, and BPE was used (basal medium), and the cells were preincubated in 5% $CO_2$ at 37° C. for 72 hours. The medium was removed and then replaced with a sample medium supplemented with resveratrol 3-O-α-glucoside to a concentration of 0.02 wt %, and the cells were cultured in 5% $CO_2$ at 37° C. After 72 hours, total RNA was extracted from the cells, and the level of expression of the sirtuin 1 gene was quantified by real time PCR. As a control group, cells were cultured without resveratrol 3-O-α-glucoside, and total RNA collected from these cells was used.

Taking as 100% the level of expression of the sirtuin 1 gene for the control group, a relative ratio of the expression level of the sirtuin 1 gene for the resveratrol 3-O-α-glucoside-supplemented group (SIRT 1 gene expression ratio, %) was determined. In the measurement of the expression level of the sirtuin 1 gene, PPIA was used for internal standard correction.

The obtained results are shown in Table 12. As is clear from Table 12, the 0.02 wt % resveratrol 3-O-α-glucoside-supplemented group was found to have a significant sirtuin 1 gene expression-promoting effect. Since it has been reported that the activation of the sirtuin gene results in various anti-aging effects, these results also confirmed that resveratrol 3-O-α-glucoside is effective against skin aging.

TABLE 12

| Resveratrol 3-O-α-Glucoside Concentration (wt %) in the Sample Solution | SIRT 1 Gene Expression Ratio (%) |
|---|---|
| 0.02 | 171 |

Example 13

Evaluation of the Sirtuin 1 Gene Expression-Promoting Effect of Resveratrol 3-O-α-Glucoside (2)

Normal human epidermal keratinocytes were seeded into 12-well culture plates at $5 \times 10^4$ cells per well. As the medium, EpiLife KG-2 medium supplemented with insulin, hEGF, hydrocortisone, anti-microbial agents, and BPE was used (basal medium), and the cells were preincubated in 5% $CO_2$ at 37° C. for 48 hours. The medium was removed, and then replaced with a sample medium obtained by removing hydrocortisone from the above-described basal medium, and by supplementing the resulting medium with resveratrol 3-O-α-glucoside to a concentration of 0.001 wt %, and the cells were cultured in 5% $CO_2$ at 37° C. For comparison, the cells were cultured under the same conditions as described above, except that resveratrol 3-O-α-glucoside in the sample medium was replaced by resveratrol 3-O-β-glucoside. After 33 hours of culture, total RNA was extracted from the cells, and the level of expression of the sirtuin 1 gene was quantified by real time PCR. As a control group, cells were cultured without resveratrol 3-O-α-glucoside or resveratrol 3-O-β-glucoside, and total RNA collected from these cells was used. Taking as 100% the level of expression of the sirtuin 1 gene for the control group, a relative ratio of the expression level of the sirtuin 1 gene for the resveratrol 3-O-α-glucoside- or resveratrol 3-O-β-glucoside-supplemented group (SIRT 1 gene expression ratio, %) was determined. In the measurement of the expression level of the sirtuin 1 gene, PPIA was used for internal standard correction.

The obtained results are shown in Table 13. From these results, the 0.001 wt % resveratrol 3-O-α-glucoside-supplemented group was found to have a significant sirtuin 1 gene expression-promoting effect. On the other hand, although the 0.001 wt % resveratrol 3-O-β-glucoside-supplemented group had a tendency to promote the sirtuin 1 gene expression, it did not show a significant difference compared to the control group. That is, these results confirmed that resveratrol 3-O-α-glucoside has an anti-aging effect remarkably higher than that of resveratrol 3-O-β-glucoside.

TABLE 13

| Test Group | SIRT 1 Gene Expression Ratio (%) |
|---|---|
| Resveratrol 3-O-α-Glucoside (0.001 wt %) | 141 |
| Resveratrol 3-O-β-Glucoside (0.001 wt %) | 120 |

Example 14

Evaluation of Matrix Metalloproteinase 9-Suppressing Effect in the Epidermis of Resveratrol 3-O-α-Glucoside Using a three-dimensional human skin model, the effect of resveratrol 3-O-α-glucoside on the matrix metalloproteinase 9 (MMP9) gene expression in the epidermis was investigated.

An aqueous solution containing resveratrol 3-O-α-glucoside at a concentration of 0.02 or 0.1 wt %, or containing resveratrol 3-O-β-glucoside at a concentration of 0.02 wt % was prepared, and the resulting solution was used as a sample solution. One-hundred microliters of the sample solution were administered to the horny layer side of the human skin model (EpiDerm EPI-200; MatTek), and cultured in 5 mL of a special medium (EPI-100-ASY) at 37° C. for 8 hours. After the culture, total RNA was extracted from the skin model, and the level of expression of the MMP9 gene was quantified by real time PCR. As a control group, distilled water was administered to a skin model instead of the sample solution, and total RNA collected from the skin model was used.

Taking as 100% the level of expression of the MMP9 gene for the control group, a relative ratio of the expression level of the MMP9 gene for the resveratrol 3-O-α-glucoside- or resveratrol 3-O-β-glucoside-supplemented group (MMP9 gene expression ratio, %) was determined. In the measurement of the expression level of the MMP9 gene, PPIA was used for internal standard correction.

The obtained results are shown in Table 14. As is clear from Table 14, the 0.02 wt % resveratrol 3-O-α-glucoside-supplemented group was found to suppress the MMP9 gene expression. On the other hand, the resveratrol 3-O-β-glucoside-supplemented group was found to promote the MMP 9 gene expression. It was thus revealed that resveratrol 3-O-α-glucoside and resveratrol 3-O-β-glucoside show mutually contradictory effects on the MMP9 expression. It was also confirmed that the MMP9 gene expression-suppressing effect of resveratrol 3-O-α-glucoside was concentration-dependent.

MMP9 is an enzyme that degrades type IV collagen present in the epidermal basement membrane. The degradation of type IV collagen is known to cause reduced firmness or elasticity, or wrinkles of the skin. These facts confirmed that resveratrol 3-O-α-glucoside, unlike other resveratrol glucosides, suppresses the expression of MMP9 to thereby suppress the degradation of type IV collagen, and thus, is expected to provide the effect of suppressing skin aging such as reduced firmness or elasticity, or wrinkles.

TABLE 14

| Test Group | MMP9 Gene Expression Ratio (%) |
|---|---|
| Resveratrol 3-O-α-Glucoside (0.02 wt %) | 85 |
| Resveratrol 3-O-α-Glucoside (0.1 wt %) | 66 |
| Resveratrol 3-O-β-Glucoside (0.02 wt %) | 124 |

Example 15

Evaluation of Matrix Metalloproteinases 1 and 9-Suppressing Effect in the Dermis of Resveratrol 3-O-α-Glucoside Using normal human dermal fibroblasts, the effect of resveratrol 3-O-α-glucoside on matrix metalloproteinase 1 (MMP1) and 9 (MMP9) genes in the dermis was investigated.

Normal human dermal fibroblasts were seeded into 12-well culture plates at $9 \times 10^4$ cells per well. As the medium, 10 vol % FBS (Fetal Bovine Serum)-containing DMEM medium (basal medium) was used, and the cells were preincubated in 5% $CO_2$ at 37° C. for 24 hours. The medium was removed and then replaced with a basal medium supplemented with 0.001 wt % of resveratrol 3-O-α-glucoside, and the cells were cultured in 5% $CO_2$ at 37° C. After 24 hours, total RNA was extracted from the cells, and the levels of expression of the MMP1 and MMP9 genes were quantified by real time PCR. As a control group, cells were cultured without resveratrol 3-O-α-glucoside, and total RNA collected from these cells was used.

Taking as 100% the level of expression of each of the MMP1 and MMP9 genes for the control group, a relative ratio of the expression level of each of the MMP1 and MMP9 genes for the resveratrol 3-O-α-glucoside-supplemented group (MMP1 and MMP9 gene expression ratios, %) was determined. In the measurement of the expression level of each of the MMP1 and MMP9 genes, GAPDH (glyceraldehyde 3-phosphate dehydrogenase) was used for internal standard correction.

The obtained results are shown in Table 15. As seen from Table 15, the 0.001 wt % resveratrol 3-O-α-glucoside-supplemented group was found to significantly suppress the expression of both the MMP1 and MMP9 genes. MMP1 is an enzyme that degrades type I collagen, which occupies most of the dermis, and greatly affects the firmness or elasticity of the dermis. The degradation of type I collagen is known to lead to reduced firmness or elasticity of the dermis. MMP9 is an enzyme that degrades type IV collagen present in the epidermal basement membrane. The degradation of type IV collagen is known to cause reduced firmness or elasticity, or wrinkles of the skin. These facts confirmed that resveratrol 3-O-α-glucoside suppresses the expression of MMP1 and MMP9 in the dermis to thereby suppress the degradation of types I and IV collagens, and thus, is expected to provide the effect of suppressing skin aging such as reduced firmness or elasticity, or wrinkles, from the dermal side as well.

TABLE 15

| Test Group | MMP1 Gene Expression Ratio (%) | MMP9 Gene Expression Ratio (%) |
| --- | --- | --- |
| Resveratrol 3-O-α-Glucoside (0.001 wt %) | 85 | 45 |

Example 16

Evaluation of the Absorption Properties of Resveratrol 3-O-α-Glucoside into the Skin Using a three-dimensional human skin model, permeabilities of resveratrol 3-O-α-glucoside and resveratrol into the skin model when administered via the skin surface were compared.

Resveratrol 3-O-α-glucoside or resveratrol (Tokyo Chemical Industry Co., Ltd.) was prepared into a 0.2 wt % solution or suspension with the addition of PBS, and the resulting solution was used as a test substance. The skin model (EPI-200X; MatTek) was loaded into a special fixture (EPI-100-FIX; MatTek), and placed in the 6-well plate of the receiver. One-hundred microliters of the test substance were added to the horny layer side, and 5 mL of PBS was added to the receiver side. After being allowed to stand at 37° C. for 20 hours, the skin model was collected, and the surface of the skin model was washed well with PBS. The skin model after being washed was homogenized in PBS. After the homogenate was centrifuged, resveratrols in the supernatant were quantified using HPLC under the same conditions as described in Production Example 1 above, and the amount of resveratrols was converted into the equivalent of agly cones.

The obtained results are shown in Table 16. These results revealed that the amount of permeation of resveratrol 3-O-α-glucoside into the skin model was 3.5 times greater than that of resveratrol, and thus, resveratrol 3-O-α-glucoside has greatly improved permeability into the skin, compared to resveratrol.

TABLE 16

| | Concentration in the Skin Model (Value Converted into the Equivalent of Aglycones, μg/cm$^2$) |
| --- | --- |
| 0.2 wt % Resveratrol 3-O-α-Glucoside | 26.5 |
| 0.2 wt % Resveratrol | 7.5 |

Example 17

Evaluation of the Absorption Properties of Resveratrol 3-O-α-Glucoside When Orally Ingested Blood concentrations of resveratrol metabolites when resveratrol 3-O-α-glucoside and resveratrol 3-O-β-glucoside were orally ingested were examined, and the absorption properties of resveratrol 3-O-α-glucoside and resveratrol 3-O-β-glucoside were compared.

To 100 mL of water, 86 mg of resveratrol 3-O-α-glucoside or resveratrol 3-O-β-glucoside (Tokyo Chemical Industry Co., Ltd.) was added, and the mixture was stirred for 1 minute. The resulting solution was orally ingested by a subject (47 years old) at a time. Blood was collected prior to, 30 minutes after, and 1, 2, 3, and 4 hours after the ingestion, and the plasma was separated by centrifugation. The test was performed three times for each of the samples. In order to quantify the amount of resveratrol derivatives in the collected plasma samples, 10 μL of β-glucronidase Type H-2 from Sigma-Aldrich Co. LLC. (glucuronidase activity: 115003 units/mL, sulfatase activity: 556 units/mL; a 5-fold diluted solution in a 100 mM acetate buffer solution (pH 5.5)) was added to 10 μL of the collected plasma, and enzyme treatment was performed at 37° C. for about 18 hours. After the reaction, 80 μL of 60% acetonitrile was added, and subsequently 100 μL of water was further added thereto, and the mixture was stirred. The filtrate obtained by filtering through a membrane (0.45 μm) was subjected to HPLC analysis. A converted resveratrol concentration was determined by converting the concentration of resveratrol derivatives in each of the plasma samples into the concentration of resveratrol, and maximum blood concentrations and areas under the curve (AUCs) 0 to 4 hours after the ingestion were determined.

<HPLC Analysis Conditions>

Column: LiChrospher RP-18 (5 μm)-packed LiChroCART 250-4 (Merck Ltd.)

Mobile phase: acetonitrile-0.2% aqueous solution of phosphoric acid (45:55, v:v) mixed solution Column temperature: 40° C.

Flow rate: 0.7 mL/min

Detection wavelength: 310 nm

Injection volume: 50 μL

The obtained results are shown in FIG. 1 and Table 17. These results revealed that resveratrol 3-O-α-glucoside has a maximum plasma concentration 3.1 times higher and an AUC 2.8 times higher than those of resveratrol 3-O-β-glucoside, and thus, has significantly improved absorption properties when orally ingested, compared to resveratrol 3-O-β-glucoside.

TABLE 17

| | Maximum Plasma Concentration (ng/mL) | Area under the Curve ((mg/L) · Hr) |
| --- | --- | --- |
| Resveratrol 3-O-α-Glucoside | 873 | 2.5 |
| Resveratrol 3-O-β-Glucoside | 282 | 0.9 |

Example 18

Evaluation of the Solubility of Resveratrol 3-O-α-Glucoside in Ethanol

Approximately 40 mg each of resveratrol 3-O-α-glucoside, resveratrol (Tokyo Chemical Industry Co., Ltd.), and resveratrol 3-O-β-glucoside (Tokyo Chemical Industry Co., Ltd.) was weighed, approximately 70 mg of a solvent (whose composition is shown in Table 18) containing ethanol (Wako Pure Chemical Industries, Ltd.) was added thereto, and the mixture was soaked in a water bath at 25° C. under light-tight conditions, and incubated for 15 hours with occasional stirring. After 15 hours, each of the samples was filtered through a 0.45 μm centrifugal filter, and then the concentration of each of the components in the filtrate was analyzed using HPLC under the same conditions as those described in Production Example 1 above. The dissolved concentration (w/v %) at 25° C. was thus determined.

The obtained results are shown in Table 18. These results revealed that in the presence of ethanol, resveratrol 3-O-α-glucoside exhibits a solubility remarkably higher than those of resveratrol and resveratrol 3-O-β-glucoside. In particular, in a solvent containing 50 w % or more of ethanol, the dissolved concentration of resveratrol 3-O-α-glucoside exceeded 30 w/v %, and resveratrol 3-O-α-glucoside was concentrated to an extremely high concentration.

TABLE 18

| Composition of Solvent Containing Ethanol | Dissolved Concentration (w/v %) at 25° C. | | |
|---|---|---|---|
| (Ethanol:Water) (Weight Ratio) | Resveratrol 3-O-α-Glucoside | Resveratrol 3-O-β-Glucoside | Resveratrol |
| 100:0 | 30 or more | 2.4 | 7.9 |
| 90:10 | 30 or more | 7.3 | 7.3 |
| 75:25 | 30 or more | 13.8 | 5.8 |
| 50:50 | 30 or more | 5.3 | 1.4 |
| 40:60 | not performed | 2.6 | 0.5 |
| 30:70 | not performed | 0.7 | 0.1 |
| 25:75 | 6.3 | 0.4 | 0.05 |
| 20:80 | not performed | 0.2 | 0.02 |
| 15:85 | 1.3 | 0.1 | 0.01 |
| 10:90 | not performed | 0.06 | 0.006 |
| 5:95 | 0.4 | 0.05 | 0.003 |
| 0:100 | 0.3 | 0.04 | 0.003 |

Example 19

Evaluation of the Solubility of Resveratrol 3-O-α-Glucoside in Glycerol

The solubility of resveratrol 3-O-α-glucoside was evaluated under the same conditions as those described in Example 18 above, except that a solvent (whose composition is shown in Table 19) containing glycerol (Wako Pure Chemical Industries, Ltd.) was used.

The obtained results are shown in Table 19. These results confirmed that resveratrol 3-O-α-glucoside exhibits a remarkably high solubility in the presence of glycerol. In particular, in a solvent containing 90 w % or more of glycerol, the dissolved concentration of resveratrol 3-O-α-glucoside exceeded 20 w/v %, and resveratrol 3-O-α-glucoside was concentrated to an extremely high concentration.

TABLE 19

| Composition of Solvent Containing Glycerol | Dissolved Concentration (w/v %) at 25° C. | | |
|---|---|---|---|
| (Glycerol:Water) (Weight Ratio) | Resveratrol 3-O-α-Glucoside | Resveratrol 3-O-β-Glucoside | Resveratrol |
| 100:0 | 30 or more | 3.1 | 0.5 |
| 90:10 | 20.8 | 1.9 | 0.3 |

TABLE 19-continued

| Composition of Solvent Containing Glycerol | Dissolved Concentration (w/v %) at 25° C. | | |
|---|---|---|---|
| (Glycerol:Water) (Weight Ratio) | Resveratrol 3-O-α-Glucoside | Resveratrol 3-O-β-Glucoside | Resveratrol |
| 75:25 | 8.7 | 1.1 | 0.1 |
| 50:50 | 2.3 | 0.3 | 0.02 |
| 25:75 | 0.7 | 0.09 | 0.007 |
| 10:90 | 0.4 | 0.05 | 0.003 |
| 0:100 | 0.3 | 0.04 | 0.003 |

Example 20

Evaluation of the Solubility of Resveratrol 3-O-α-Glucoside in Propylene Glycol

The solubility of resveratrol 3-O-α-glucoside was evaluated under the same conditions as those described in Example 18 above, except that a solvent (whose composition is shown in Table 20) containing propylene glycol (Wako Pure Chemical Industries, Ltd.) was used.

The obtained results are shown in Table 20. These results also confirmed that in the presence of propylene glycol, resveratrol 3-O-α-glucoside exhibits a solubility remarkably higher than those of resveratrol and resveratrol 3-O-β-glucoside. In particular, in a solvent containing 75 w % or more of propylene glycol, the dissolved concentration of resveratrol 3-O-α-glucoside exceeded 30 w/v %, and resveratrol 3-O-α-glucoside was concentrated to an extremely high concentration.

TABLE 20

| Composition of Solvent Containing Propylene Glycol | Dissolved Concentration (w/v %) at 25° C. | | |
|---|---|---|---|
| (Propylene Glycol:Water) (Weight Ratio) | Resveratrol 3-O-α-Glucoside | Resveratrol 3-O-β-Glucoside | Resveratrol |
| 100:0 | 30 or more | 11.3 | 7.0 |
| 90:10 | 30 or more | 12.5 | 4.8 |
| 75:25 | 30 or more | 11.5 | 2.6 |
| 50:50 | 21.9 | 3.3 | 0.4 |
| 25:75 | 2.7 | 0.2 | 0.03 |
| 20:80 | not performed | 0.1 | not performed |
| 15:85 | not performed | 0.09 | not performed |
| 10:90 | 0.6 | 0.06 | 0.006 |
| 5:95 | not performed | 0.04 | 0.004 |
| 0:100 | 0.3 | 0.04 | 0.003 |

Example 21

Evaluation of the Solubility of Resveratrol 3-O-α-Glucoside in 1,3-Butylene Glycol The solubility of resveratrol 3-O-α-glucoside was evaluated under the same conditions as those described in Example 18 above, except that a solvent (whose composition is shown in Table 21) containing 1,3-butylene glycol (Wako Pure Chemical Industries, Ltd.) was used.

The obtained results are shown in Table 21. These results also confirmed that in the presence of 1,3-butylene glycol, resveratrol 3-O-α-glucoside exhibits a remarkably high solubility. In particular, in a solvent containing 50 w % or more of 1,3-butylene glycol, the dissolved concentration of resveratrol 3-O-α-glucoside exceeded 20 w/v %, and resveratrol 3-O-α-glucoside was concentrated to an extremely high concentration.

TABLE 21

| Composition of Solvent Containing 1,3-Butylene Glycol (1,3-Butylene Glycol:Water) (Weight Ratio) | Dissolved Concentration (w/v %) at 25° C. | | |
|---|---|---|---|
| | Resveratrol 3-O-α-Glucoside | Resveratrol 3-O-β-Glucoside | Resveratrol |
| 100:0 | 30 or more | 7.2 | 7.8 |
| 90:10 | 30 or more | 9.7 | 5.7 |
| 75:25 | 30 or more | 7.5 | 3.5 |
| 50:50 | 22.2 | 2.8 | 0.5 |
| 25:75 | 4.5 | 0.3 | 0.04 |
| 20:80 | not performed | 0.2 | not performed |
| 15:85 | not performed | 0.1 | not performed |
| 10:90 | 0.8 | 0.07 | 0.008 |
| 5:95 | not performed | 0.04 | 0.004 |
| 0:100 | 0.3 | 0.04 | 0.003 |

Example 22

Evaluation of the Solubility of Resveratrol 3-O-α-Glucoside in Dipropylene Glycol The solubility of resveratrol 3-O-α-glucoside was evaluated under the same conditions as those described in Example 18 above, except that a solvent (whose composition is shown in Table 22) containing dipropylene glycol (Asahi Glass Co., Ltd.) was used.

The obtained results are shown in Table 22. These results also confirmed that in the presence of dipropylene glycol, resveratrol 3-O-α-glucoside exhibits a remarkably high solubility. In particular, in a solvent containing 50 w % or more of dipropylene glycol, the dissolved concentration of resveratrol 3-O-α-glucoside exceeded 30 w/v %, and resveratrol 3-O-α-glucoside was concentrated to an extremely high concentration.

TABLE 22

| Composition of Solvent Containing Dipropylene Glycol (Dipropylene Glycol:Water) (Weight Ratio) | Dissolved Concentration (w/v %) at 25° C. | | |
|---|---|---|---|
| | Resveratrol 3-O-α-Glucoside | Resveratrol 3-O-β-Glucoside | Resveratrol |
| 100:0 | 30 or more | 15.0 | 14.7 |
| 90:10 | 30 or more | 23.9 | 15.3 |
| 75:25 | 30 or more | 26.1 | 17.8 |
| 50:50 | 30 or more | 11.5 | 4.6 |
| 25:75 | 17.8 | 0.9 | 0.2 |
| 20:80 | not performed | 0.5 | not performed |
| 15:85 | not performed | 0.3 | not performed |
| 10:90 | 1.9 | 0.1 | 0.01 |
| 5:95 | not performed | 0.06 | 0.006 |
| 0:100 | 0.3 | 0.04 | 0.003 |

Example 23

Evaluation of the Solubility of Resveratrol 3-O-α-Glucoside in 1,2-Pentanediol

The solubility of resveratrol 3-O-α-glucoside was evaluated under the same conditions as those described in Example 18 above, except that a solvent (whose composition is shown in Table 23) containing 1,2-pentanediol (Kankosha Co., Ltd.) was used.

The obtained results are shown in Table 23. These results also confirmed that in the presence of 1,2-pentanediol, resveratrol 3-O-α-glucoside exhibits a remarkably high solubility. In particular, in a solvent containing 25 w % or more of 1,2-pentanediol, the dissolved concentration of resveratrol 3-O-α-glucoside exceeded 20 w/v %, and resveratrol 3-O-α-glucoside was concentrated to an extremely high concentration.

TABLE 23

| Composition of Solvent Containing 1,2-Pentanediol (1,2-Pentanediol:Water) (Weight Ratio) | Dissolved Concentration (w/v %) at 25° C. | | |
|---|---|---|---|
| | Resveratrol 3-O-α-Glucoside | Resveratrol 3-O-β-Glucoside | Resveratrol |
| 100:0 | 30 or more | 4.6 | 4.1 |
| 90:10 | 30 or more | 9.4 | 4.8 |
| 75:25 | 30 or more | 11.3 | 4.0 |
| 50:50 | 30 or more | 7.5 | 2.4 |
| 25:75 | 21.2 | 2.3 | 0.4 |
| 10:90 | 3.1 | 0.2 | 0.02 |
| 0:100 | 0.3 | 0.04 | 0.003 |

Example 24

Evaluation of the Solubility of Resveratrol 3-O-α-Glucoside in 1,2-Hexanediol

The solubility of resveratrol 3-O-α-glucoside was evaluated under the same conditions as those described in Example 18 above, except that a solvent (whose composition is shown in Table 24) containing 1,2-hexanediol (Kankosha Co., Ltd.) was used.

The obtained results are shown in Table 24. These results also confirmed that in the presence of 1,2-hexanediol, resveratrol 3-O-α-glucoside exhibits a remarkably high solubility. In particular, in a solvent containing 25 w % or more of 1,2-hexanediol, the dissolved concentration of resveratrol 3-O-α-glucoside exceeded 25 w/v %, and resveratrol 3-O-α-glucoside was concentrated to an extremely high concentration.

TABLE 24

| Composition of Solvent Containing 1,2-Hexanediol (1,2-Hexanediol:Water) (Weight Ratio) | Dissolved Concentration (w/v %) at 25° C. | | |
|---|---|---|---|
| | Resveratrol 3-O-α-Glucoside | Resveratrol 3-O-β-Glucoside | Resveratrol |
| 100:0 | 29.7 | 3.2 | 3.3 |
| 90:10 | 30 or more | 10.7 | 5.1 |
| 75:25 | 30 or more | 7.9 | 3.3 |
| 50:50 | 30 or more | 6.5 | 2.2 |

TABLE 24-continued

| Composition of Solvent Containing 1,2-Hexanediol (1,2-Hexanediol:Water) (Weight Ratio) | Dissolved Concentration (w/v %) at 25° C. | | |
|---|---|---|---|
| | Resveratrol 3-O-α-Glucoside | Resveratrol 3-O-β-Glucoside | Resveratrol |
| 25:75 | 30 or more | 2.6 | 0.7 |
| 10:90 | 8.2 | 0.5 | 0.08 |
| 5:95 | not performed | 0.1 | not performed |
| 0:100 | 0.3 | 0.04 | 0.003 |

Referential Example 1

Evaluation of the Solubility of Resveratrol 3-O-α-Glucoside in Water

Approximately 5 mg each of resveratrol 3-O-α-glucoside, resveratrol (Tokyo Chemical Industry Co., Ltd.), and resveratrol 3-O-β-glucoside (Tokyo Chemical Industry Co., Ltd.) was weighed, approximately 1 mL of water was added thereto, and the mixture was soaked in a water bath at 25° C. under light-tight conditions, and incubated for 20 hours with occasional stirring. After 20 hours, each of the samples was filtered through a 0.45 μm centrifugal filter, and then the concentration of each of the components in the filtrate was analyzed using HPLC under the same conditions as those described in Production Example 1 above. The dissolved concentration (w/v %) in water at 25° C. was thus determined.

The obtained results are shown in Table 25. These results confirmed that resveratrol 3-O-α-glucoside exhibits an extremely high water solubility, compared to not only resveratrol but also resveratrol 4'-O-α-glucoside, which is similarly in the a-form, and resveratrol 3-O-β-glucoside, which is similarly a 3-position glycoside. That is, it was revealed that the physical properties of the resveratrol glucosides greatly vary depending on the form of the resveratrol-glucose bond.

TABLE 25

| | Dissolved Concentration (μg/mL) in Water |
|---|---|
| Resveratrol 3-O-α-Glucoside | 2900 |
| Resveratrol 4'-O-α-Glucoside | 150 |
| Resveratrol 3-O-β-Glucoside | 370 |
| Resveratrol | 30 |

Referential Example 2

Evaluation of the Stability of Resveratrol 3-O-α-Glucoside in Water

Each of resveratrol 3-O-α-glucoside (produced in Production Example 1), resveratrol (Tokyo Chemical Industry Co., Ltd.), and resveratrol 4'-O-α-glucoside (produced in Production Example 1) was dissolved in a 30 vol % aqueous solution of ethanol to a concentration of 2 mM, and the solution was stored at 40° C. under light-tight conditions. The coloration of the solution after being stored for 6 months was visually observed. Further, absorbances at 430 nm of the solution before and after the storage were measured, and the residual amount of each of the components in the solution was analyzed using HPLC. HPLC was performed under the same conditions as those described in Production Example 1.

The obtained results are shown in Table 26. These results revealed that resveratrol 3-O-α-glucoside is still colorless and shows a high residual content even after storage, and is thus superior to resveratrol and resveratrol 4'-O-α-glucoside in terms of storage stability in the presence of water.

TABLE 26

| | Coloration | | |
|---|---|---|---|
| | Visual Observation | Difference between Absorbances at 430 nm (Δ A 430) before and after Storage | Residual Content (%) |
| Resveratrol 3-O-α-Glucoside | colorless | 0.03 | 93 |
| Resveratrol 4'-O-α-Glucoside | slightly colored (brown) | 0.21 | 86 |
| Resveratrol | strongly colored (brown) | 1.36 | 60 |

The invention claimed is:

1. A method for reducing the effects of aging on the skin comprising a step of percutaneously or orally administering resveratrol 3-O-α-glucoside to a human in need thereof, wherein:
    a daily amount of about 1 to 2000 mg of resveratrol 3-O-α-glucoside is orally administered or ingested, or
    a daily amount of about 0.5 to 100 μg of resveratrol 3-O-α-glucoside per $cm^2$ of the skin is percutaneously administered.

2. The method according to claim 1, wherein the human is in need of suppressing melanogenesis, and pigmentation is suppressed by percutaneous or oral administration of the resveratrol 3-O-α-glucoside.

3. The method according to claim 1, wherein the human is in need of inhibiting a hyaluronidase in dermis layer or suppressing a matrix metalloproteinase expression, and degradation of hyaluronic acid or collagen in dermis layer is suppressed by percutaneous or oral administration of the resveratrol 3-O-α-glucoside.

4. The method according to claim 1, wherein the human is in need of reducing oxidative stress in skin tissue, and oxidative stress in skin tissue is reduced by percutaneous or oral administration of the resveratrol 3-O-α-glucoside.

5. The method according to claim 1, wherein the human is in need of activating skin cells, and decrease of skin function is suppressed by percutaneous or oral administration of the resveratrol 3-O-α-glucoside.

6. The method according to claim 1, wherein the human is in need of suppressing sirtuin gene expression, and sirtuin gene expression is suppressed by percutaneous or oral administration of the resveratrol 3-O-α-glucoside.

7. The method according to claim 1, wherein the human is in need of suppressing inflammation, and acceleration of aging is suppressed by percutaneous or oral administration of the resveratrol 3-O-α-glucoside.

* * * * *